US007155746B2

(12) United States Patent
Schorr et al.

(10) Patent No.: US 7,155,746 B2
(45) Date of Patent: Jan. 2, 2007

(54) ANTI-WICKING PROTECTIVE WORKWEAR AND METHODS OF MAKING AND USING SAME

(75) Inventors: Phillip Andrew Schorr, Atlanta, GA (US); Lee Kirby Jameson, Roswell, GA (US); Varunesh Sharma, Atlanta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 31 days.

(21) Appl. No.: 10/330,514

(22) Filed: Dec. 27, 2002

(65) Prior Publication Data

US 2004/0123367 A1 Jul. 1, 2004

(51) Int. Cl.
*A41D 13/12* (2006.01)
(52) U.S. Cl. .................................. 2/51; 2/125
(58) Field of Classification Search ............... 2/51, 2/125, 126, 123, 114, 457, 456, 16, 48, 77, 2/85, 87, 93, 115, 901, 108, 135, 244, 275, 2/46, 49.1, 50, 49.4, 69, 82, 118, 120, 159, 2/161.6, 161.7, 161.8, 167, 243.1, 59, 60, 2/455, 162; 128/846, 849, 853, 855, 856; 442/79, 85, 86
See application file for complete search history.

(56) References Cited

U.S. PATENT DOCUMENTS

| 3,338,992 | A | 8/1967 | Kinney |
| 3,341,394 | A | 9/1967 | Kinney |
| 3,502,763 | A | 3/1970 | Hartmann |
| 3,542,615 | A | 11/1970 | Dobo et al. |
| 3,692,618 | A | 9/1972 | Dorschner et al. |
| 3,802,817 | A | 4/1974 | Matsuki et al. |
| RE28,219 | E | 10/1974 | Taylor et al. |
| 3,849,241 | A | 11/1974 | Butin et al. |
| 3,855,046 | A | 12/1974 | Hansen et al. |
| 3,868,728 | A | * | 3/1975 | Krzewinski ............. 2/114 |
| 4,041,203 | A | 8/1977 | Brock et al. |
| 4,171,542 | A | * | 10/1979 | Cox et al. ............... 2/51 |
| 4,303,924 | A | 12/1981 | Young, Jr. |
| 4,340,563 | A | 7/1982 | Appel et al. |
| 4,374,888 | A | 2/1983 | Bornslaeger |
| 4,382,262 | A | 5/1983 | Savit |
| 4,389,503 | A | 6/1983 | Maxwell et al. |
| 4,389,734 | A | * | 6/1983 | Franz et al. ............. 2/59 |
| 4,478,910 | A | 10/1984 | Oshima et al. |
| 4,503,444 | A | 3/1985 | Tacklind |
| 4,504,357 | A | 3/1985 | Holbein et al. |
| 4,504,977 | A | * | 3/1985 | King et al. ............. 2/51 |

(Continued)

FOREIGN PATENT DOCUMENTS

DE 2313335 1/1975

(Continued)

OTHER PUBLICATIONS

RD 173017, Sep. 10, 1978, (abstract).

(Continued)

*Primary Examiner*—A. Vanatta
(74) *Attorney, Agent, or Firm*—Steven D. Flack; Richard M. Shane

(57) ABSTRACT

The present invention relates to protective outerwear for covering a body portion. The protective outerwear has an inside surface and an outside surface, with at least the outside surface including thereupon an ink jet printed low surface tension liquid blocking material in a continuous unbroken band, region, or combination of such, for blocking the wicking of liquid that is contained on the outside surface of the outerwear.

25 Claims, 11 Drawing Sheets

U.S. PATENT DOCUMENTS

| | | | |
|---|---|---|---|
| 4,526,825 A | 7/1985 | Whitehead | |
| 4,535,481 A | 8/1985 | Ruth-Larson et al. | |
| 4,689,078 A | 8/1987 | Koike et al. | |
| 4,752,972 A | 6/1988 | Neckerman et al. | |
| 4,786,288 A | 11/1988 | Handa et al. | |
| 4,835,208 A | 5/1989 | Ball | |
| 4,841,310 A | 6/1989 | Hoffman | |
| 4,849,770 A | 7/1989 | Koike et al. | |
| 4,909,879 A | 3/1990 | Ball | |
| 4,969,951 A | 11/1990 | Koike et al. | |
| 4,991,232 A * | 2/1991 | Taylor | 2/51 |
| 5,003,902 A * | 4/1991 | Benstock et al. | 112/418 |
| 5,019,066 A | 5/1991 | Freeland et al. | |
| 5,070,540 A * | 12/1991 | Bettcher et al. | 2/2.5 |
| 5,087,283 A | 2/1992 | Dixon et al. | |
| 5,116,682 A | 5/1992 | Chakravarti et al. | |
| 5,145,727 A | 9/1992 | Potts et al. | |
| 5,151,321 A | 9/1992 | Reeves et al. | |
| 5,169,706 A | 12/1992 | Collier, IV et al. | |
| 5,178,931 A | 1/1993 | Perkins et al. | |
| 5,188,885 A | 2/1993 | Timmons et al. | |
| 5,195,950 A | 3/1993 | Delannoy | |
| 5,213,881 A | 5/1993 | Timmons et al. | |
| 5,214,442 A | 5/1993 | Roller | |
| 5,271,883 A | 12/1993 | Timmons et al. | |
| 5,280,310 A | 1/1994 | Otsuka et al. | |
| 5,371,520 A | 12/1994 | Kubota | |
| 5,444,871 A * | 8/1995 | Lopez | 2/114 |
| 5,458,590 A | 10/1995 | Schleinz et al. | |
| 5,461,724 A * | 10/1995 | Wiedner et al. | 2/457 |
| 5,464,688 A | 11/1995 | Timmons et al. | |
| 5,466,232 A | 11/1995 | Cadieux et al. | |
| 5,481,281 A | 1/1996 | Otsuka et al. | |
| 5,487,614 A | 1/1996 | Hale | |
| 5,499,400 A * | 3/1996 | Masuda et al. | 2/161.6 |
| 5,503,076 A | 4/1996 | Yeo | |
| 5,538,550 A | 7/1996 | Yaegashi et al. | |
| 5,562,037 A | 10/1996 | Schleinz et al. | |
| 5,563,642 A | 10/1996 | Keefe et al. | |
| 5,566,616 A | 10/1996 | Schleinz et al. | |
| 5,571,586 A | 11/1996 | Gobran | |
| 5,586,339 A | 12/1996 | Lathan | |
| 5,591,153 A | 1/1997 | Mattingly, III | |
| 5,594,955 A | 1/1997 | Sommers | |
| 5,597,642 A | 1/1997 | Schleinz et al. | |
| 5,628,067 A * | 5/1997 | Meyer et al. | 2/125 |
| 5,629,063 A | 5/1997 | Gobran | |
| 5,648,805 A | 7/1997 | Keefe et al. | |
| 5,670,004 A | 9/1997 | Mattingly, III | |
| 5,673,433 A * | 10/1997 | Rothrum | 2/46 |
| 5,681,645 A | 10/1997 | Strack et al. | |
| 5,694,739 A | 12/1997 | Mattingly, III | |
| 5,695,855 A | 12/1997 | Yeo et al. | |
| 5,695,868 A | 12/1997 | McCormack | |
| 5,705,251 A | 1/1998 | Morman et al. | |
| 5,720,738 A | 2/1998 | Clark | |
| 5,755,906 A | 5/1998 | Achter et al. | |
| 5,759,673 A | 6/1998 | Ikezawa et al. | |
| 5,762,642 A | 6/1998 | Coles et al. | |
| 5,769,837 A | 6/1998 | Parr | |
| 5,784,279 A | 7/1998 | Barlage, III et al. | |
| H1746 H | 8/1998 | Carrier et al. | |
| 5,793,398 A | 8/1998 | Hennig | |
| 5,797,894 A | 8/1998 | Cadieux et al. | |
| 5,807,365 A | 9/1998 | Luceri | |
| 5,843,254 A | 12/1998 | Clark | |
| 5,851,274 A | 12/1998 | Lin | |
| 5,851,595 A | 12/1998 | Jones, Jr. | |
| 5,853,859 A | 12/1998 | Levy et al. | |
| 5,855,999 A | 1/1999 | McCormack | |
| 5,895,505 A | 4/1999 | Yamamoto et al. | |
| 5,919,539 A | 7/1999 | Bisbis et al. | |
| 5,931,824 A | 8/1999 | Stewart et al. | |
| 5,972,082 A | 10/1999 | Koyano et al. | |
| 5,985,396 A | 11/1999 | Kerins et al. | |
| 6,013,347 A | 1/2000 | Martin et al. | |
| 6,020,405 A | 2/2000 | Matzinger et al. | |
| 6,024,220 A | 2/2000 | Smith et al. | |
| 6,033,065 A | 3/2000 | Ikezaki | |
| 6,037,281 A | 3/2000 | Mathis et al. | |
| 6,040,251 A * | 3/2000 | Caldwell | 442/123 |
| 6,050,666 A | 4/2000 | Yeoh et al. | |
| 6,051,036 A | 4/2000 | Kusaki et al. | |
| 6,096,412 A | 8/2000 | McFarland et al. | |
| 6,103,364 A | 8/2000 | Harris et al. | |
| 6,106,922 A | 8/2000 | Cejka et al. | |
| 6,120,888 A | 9/2000 | Dolsey et al. | |
| 6,132,858 A | 10/2000 | Kloos | |
| 6,141,799 A | 11/2000 | Morris | |
| 6,142,984 A | 11/2000 | Brown et al. | |
| 6,146,770 A | 11/2000 | Sargeant et al. | |
| 6,149,259 A | 11/2000 | Otsuka et al. | |
| 6,150,005 A | 11/2000 | Williams et al. | |
| 6,159,581 A | 12/2000 | Yoneda et al. | |
| 6,183,587 B1 | 2/2001 | McFall et al. | |
| 6,199,968 B1 | 3/2001 | Katakura et al. | |
| 6,231,652 B1 | 5/2001 | Koyano et al. | |
| 6,235,098 B1 | 5/2001 | Maekawa et al. | |
| 6,235,659 B1 | 5/2001 | McAmish et al. | |
| 6,245,410 B1 | 6/2001 | Hahnle et al. | |
| 6,254,582 B1 | 7/2001 | O'Donnell et al. | |
| 6,258,427 B1 | 7/2001 | Kerins et al. | |
| 6,263,816 B1 | 7/2001 | Codos et al. | |
| 6,265,053 B1 | 7/2001 | Kronzer et al. | |
| 6,266,436 B1 | 7/2001 | Bett et al. | |
| H1978 H | 8/2001 | Freiburger et al. | |
| 6,276,790 B1 | 8/2001 | Ikezaki | |
| 6,286,144 B1 * | 9/2001 | Henderson et al. | 2/69 |
| 6,316,688 B1 | 11/2001 | Hammons et al. | |
| 6,328,793 B1 | 12/2001 | Malhotra et al. | |
| 6,395,957 B1 | 5/2002 | Chen et al. | |
| 6,497,789 B1 | 12/2002 | Hermans et al. | |
| 6,530,090 B1 * | 3/2003 | Ambrose et al. | 2/59 |
| 6,539,866 B1 | 4/2003 | Osawa et al. | |
| 6,699,360 B1 | 3/2004 | Heath et al. | |
| 6,851,125 B1 | 2/2005 | Fujikawa et al. | |
| 6,941,579 B1 * | 9/2005 | Tanenbaum | 2/123 |
| 2001/0053643 A1 | 12/2001 | McAmish et al. | |
| 2002/0007834 A1 | 1/2002 | Trotter et al. | |
| 2002/0060728 A1 | 5/2002 | Koizumi et al. | |
| 2002/0075343 A1 | 6/2002 | Classens et al. | |
| 2003/0079272 A1* | 5/2003 | Poppe | 2/114 |

FOREIGN PATENT DOCUMENTS

| | | |
|---|---|---|
| DE | 2340855 | 6/1975 |
| DE | 2654823 | 6/1978 |
| DE | 2412852 | 5/1979 |
| DE | 19803827 | 8/1999 |
| DE | 19810847 | 9/1999 |
| DE | 19810849 | 5/2000 |
| EP | 0 023 433 | 2/1981 |
| EP | 0 211 524 | 2/1987 |
| EP | 0 471 384 | 2/1992 |
| EP | 0 575 204 | 6/1993 |
| EP | 0 336 043 | 7/1993 |
| EP | 0 571 127 | 11/1993 |
| EP | 0 639 459 | 2/1995 |
| EP | 0 713 774 | 5/1996 |
| EP | 0 304 957 | 11/1996 |
| EP | 0 747 029 | 12/1996 |
| EP | 0 764 550 | 3/1997 |
| EP | 0 805 027 | 11/1997 |
| EP | 0 604 729 | 3/1998 |

| | | | | | | |
|---|---|---|---|---|---|---|
| EP | 0 809 680 | 12/1998 | | JP | 09-286 102 A2 | 11/1997 |
| EP | 1 059 340 | 12/2000 | | JP | 09-314 984 A2 | 12/1997 |
| EP | 1 070 596 | 1/2001 | | JP | 10-034 967 A2 | 2/1998 |
| EP | 0 777 008 | 4/2001 | | JP | 10-044 408 A2 | 2/1998 |
| EP | 1 164 007 | 12/2001 | | JP | 2 732 999 B2 | 3/1998 |
| EP | 1 186 431 | 3/2002 | | JP | 2 758 788 B2 | 5/1998 |
| EP | 0 861 154 | 4/2002 | | JP | 10-138 504 A2 | 5/1998 |
| EP | 1 062 095 | 6/2002 | | JP | 10-138 510 A2 | 5/1998 |
| EP | 1 224 876 | 7/2002 | | JP | 10-138 516 A2 | 5/1998 |
| FR | 2741296 | 5/1997 | | JP | 10-138 520 A2 | 5/1998 |
| GB | 2 128 439 | 4/1984 | | JP | 10-138 521 A2 | 5/1998 |
| GB | 2 334 684 | 9/1999 | | JP | 10-193 610 A2 | 7/1998 |
| JP | 55-051 583 A2 | 4/1980 | | JP | 10-264 498 A2 | 10/1998 |
| JP | 57-115 352 A2 | 7/1982 | | JP | 10-278 312 A2 | 10/1998 |
| JP | 60-104 076 A2 | 6/1985 | | JP | 11-010 852 A2 | 1/1999 |
| JP | 85-027 588 B | 6/1985 | | JP | 11-010 853 A2 | 1/1999 |
| JP | 60-169 489 A2 | 9/1985 | | JP | 11-061 021 A2 | 3/1999 |
| JP | 60-245 557 A2 | 12/1985 | | JP | 11-099 646 A2 | 4/1999 |
| JP | 61-118 473 A2 | 6/1986 | | JP | 11-188 968 A2 | 7/1999 |
| JP | 61-179 269 A2 | 8/1986 | | JP | 11-207 951 A2 | 8/1999 |
| JP | 61-179 271 A2 | 8/1986 | | JP | 11-268 284 A2 | 10/1999 |
| JP | 61-179 272 A2 | 8/1986 | | JP | 11-268 405 A2 | 10/1999 |
| JP | 61-179 273 A2 | 8/1986 | | JP | 11-277 772 A2 | 10/1999 |
| JP | 63-265 680 A2 | 11/1988 | | JP | 2000-000 266 A | 1/2000 |
| JP | 01-013 518 A2 | 1/1989 | | JP | 2000-043 401 A2 | 2/2000 |
| JP | 03-104 646 A2 | 5/1991 | | JP | 2000-052 640 A2 | 2/2000 |
| JP | 03-049 311 B4 | 7/1991 | | JP | 2000-127 611 A2 | 5/2000 |
| JP | 92-015 746 B | 3/1992 | | JP | 2000-190 628 A2 | 7/2000 |
| JP | 04-251747 A | 9/1992 | | JP | 2000-203 150 A2 | 7/2000 |
| JP | 04-292 947 A2 | 10/1992 | | JP | 2000-233 571 A2 | 8/2000 |
| JP | 05-035 191 B4 | 5/1993 | | JP | 3 089 308 B2 | 9/2000 |
| JP | 05-230 409 A2 | 9/1993 | | JP | 3 089 583 B2 | 9/2000 |
| JP | 05-247 390 A2 | 9/1993 | | JP | 2000-238 410 A2 | 9/2000 |
| JP | 05-331 396 A2 | 12/1993 | | JP | 2000-256 974 A2 | 9/2000 |
| JP | 06-127 032 A2 | 5/1994 | | JP | 2000-296 670 A | 10/2000 |
| JP | 06-246 934 A2 | 9/1994 | | JP | 2001-010 031 A2 | 1/2001 |
| JP | 06-286 134 A2 | 10/1994 | | JP | 2001 018 518 A2 | 1/2001 |
| JP | 06-312 509 A2 | 11/1994 | | JP | 2001 020 185 A2 | 1/2001 |
| JP | 07-034 019 A2 | 2/1995 | | JP | 2001 039 017 A2 | 2/2001 |
| JP | 07-068 922 A2 | 3/1995 | | NL | 9400024 A | 8/1995 |
| JP | 07-089 077 A2 | 4/1995 | | WO | 95/02973 | 2/1995 |
| JP | 07-125 197 A2 | 5/1995 | | WO | WO 95/15410 | 6/1995 |
| JP | 07-156 407 A2 | 6/1995 | | WO | 96/31345 | 10/1996 |
| JP | 07-213 310 A | 8/1995 | | WO | WO 97/18090 | 5/1997 |
| JP | 07-241 983 A2 | 9/1995 | | WO | WO 98/43821 | 10/1998 |
| JP | 07-304 167 A2 | 11/1995 | | WO | WO 99/33669 | 7/1999 |
| JP | 07-314 694 A2 | 12/1995 | | WO | WO 99/43760 | 9/1999 |
| JP | 07-314 728 A2 | 12/1995 | | WO | WO 99/55269 | 11/1999 |
| JP | 07-323 657 A2 | 12/1995 | | WO | WO 99/55270 | 11/1999 |
| JP | 08-052 903 A2 | 2/1996 | | WO | WO 99/55271 | 11/1999 |
| JP | 08-118 617 A2 | 5/1996 | | WO | WO 99/60973 | 12/1999 |
| JP | 08-164 602 A2 | 6/1996 | | WO | WO 99/65700 | 12/1999 |
| JP | 08-174 995 A2 | 7/1996 | | WO | WO 00/07426 | 2/2000 |
| JP | 08-187 933 A2 | 7/1996 | | WO | WO 00/35401 | 6/2000 |
| JP | 08-216 395 A2 | 8/1996 | | WO | WO 00/40195 | 7/2000 |
| JP | 08-259 868 A2 | 10/1996 | | WO | WO 00/40196 | 7/2000 |
| JP | 08-267 733 A2 | 10/1996 | | WO | WO 00/42960 | 7/2000 |
| JP | 08-309 987 A2 | 11/1996 | | WO | WO 00/56972 | 9/2000 |
| JP | 09-031 866 A2 | 2/1997 | | WO | WO 00/69950 | 11/2000 |
| JP | 09-039 233 A2 | 2/1997 | | WO | WO 00/72984 | 12/2000 |
| JP | 2 593 830 B2 | 3/1997 | | WO | WO 00/73063 | 12/2000 |
| JP | 09-057 966 A2 | 3/1997 | | WO | WO 00/76441 | 12/2000 |
| JP | 09-066 661 A2 | 3/1997 | | WO | 01/03529 | 1/2001 |
| JP | 2 618 359 B2 | 6/1997 | | WO | WO 01/02254 | 1/2001 |
| JP | 09-175 004 A2 | 7/1997 | | WO | WO 01/27382 | 4/2001 |
| JP | 09-175 005 A2 | 7/1997 | | WO | WO 01/31122 | 5/2001 |
| JP | 09-175 006 A2 | 7/1997 | | WO | WO 01/31124 | 5/2001 |
| JP | 09-175 007 A2 | 7/1997 | | WO | WO 01/32318 | 5/2001 |
| JP | 09-194 781 A2 | 7/1997 | | WO | WO 01/36171 | 5/2001 |
| JP | 09-226 229 A2 | 9/1997 | | WO | WO 01/36209 | 5/2001 |
| JP | 09-240 138 A2 | 9/1997 | | WO | WO 01/49230 | 7/2001 |
| JP | 09-268 482 A2 | 10/1997 | | WO | WO 01/50412 | 7/2001 |
| JP | 09-268 484 A | 10/1997 | | WO | WO 02/14080 | 2/2002 |

| | | |
|---|---|---|
| WO | WO 02/051644 | 7/2002 |
| WO | 03/037121 | 5/2003 |

OTHER PUBLICATIONS

Pages 198-201 of Ink Jet Technology and Product Development Strategies, by Stephen F. Pond, copyright 2000, of Torrey Pines Research.

Material Safety Data Sheet; Hot Melt Ink, Cyan, Magenta, Yellow, etc.; pp. 1-3.

Material Safety Data Sheet; Hot Melt Ink, Black, High; JET 7520/JET 7533; pp. 1-4.

Sales Literature; Oct. 1, 2002; Spectra Inc.; "Galaxy PH 256/80 HM".

Hydrophobic Surfaces, edited by F. M. Fowkes of the Academic Press, New York, 1969, pp. 1-27.

Introduction to Colloid and Surface Chemistry by Duncan J. Shaw, Third Edition, Butterworths 1980, pp. 131-135.

Pages 377-385 of Ink Jet Technology and Product Development Strategies, by Stephen F. Pond, copyright 2000, of Torrey Pines Research.

ASTM Designation: F1571-95, "Standard Test Method for Determination of Abrasion and Smudge Resistance of Images Produced from Business Copy Products", Nov. 1995, pp. 1409-1412.

AATCC Evaluation Procedure 8, AATCC 9-Step Chromatic Transference Scale, AATCC Technical Manual, 1999, pp. 378-379.

Pocket Guide to Color Reproduction, Communication and Control, by Miles Southworth (1972), pp. 1-7.

\* cited by examiner

FIG 5 (A)-(D)

ANTI-WICKING PROTECTIVE WORKWEAR AND METHODS OF MAKING AND USING SAME

TECHNICAL FIELD

The present invention pertains to protective workwear. More specifically, the present invention pertains to medical gowns, surgical gowns and other protective workwear that offer additional contamination protection to users of such workwear, and methods of making and using the same.

BACKGROUND OF THE INVENTION

With the burgeoning costs of medical care, and the sterilization costs associated with cleansing medical supplies that may have been exposed to blood borne pathogens and other contaminants, manufacturers of medical supplies such as medical equipment and protective medical apparel, have sought to reduce costs of such supplies to medical service providers. In this regard, medical supply manufacturers have turned to the production of disposable medical supplies so as to reduce the medical costs (in time and labor) associated with cleaning and sterilization, and to provide enhanced options to medical service providers for products that need not be reused. For the purposes of this application, the term "medical service provider" is meant to encompass all persons who treat either human or animal patients through the course of their employment or otherwise, or are exposed to blood or other types of low surface tension liquids containing potentially harmful components or contaminants, during the course of their employment or otherwise.

Further, with the onset of the autoimmune deficiency syndrome (HIV virus) and other blood borne pathogens, such as hepatitis, there has been a concentrated effort to provide medical service providers with barrier protection to such viruses. To this end, protective workwear used in medical procedures (medical garments), such as hospital and surgical gowns, have been made from nonwoven materials instead of traditional woven materials, such as cotton and linen-based fabrics.

In particular, cloth-like multi-layered fibrous nonwoven laminates, films or film laminates, and film and fibrous nonwoven laminate composites, have been produced that offer barrier protection when employed as medical garment material. Such materials have proven in some circumstances, to be liquid-impervious, but breathable. For instance, if such garment materials are made from only fibrous nonwoven materials and/or breathable films, such materials have allowed the passage of gasses/vapors in order to provide the necessary thermal comfort to medical personnel, but without sacrificing high levels of protection. If such garments are made from monolithic films (without pores) or film composites, such garments may often be uncomfortable to wear for an extended period as they restrict the ability of air to easily pass through them. If such garments are made of fibrous material, but are additionally coated with certain film-like coatings to provide a moisture barrier, such materials are likewise uncomfortable to wear. For instance, it is known to coat large portions of hospital or surgeon's garments in the arm and abdominal areas. While such garments may provide high barriers to liquids that may be present in a hospital setting, such garments are often uncomfortable since they fail to breathe in these same large protected areas. Further, if large areas of such garments are coated with a liquid barrier, such film coating may fail to provide the necessary coefficient of friction which is required for the sustained placement of a glove over such materials, as is the practice in a hospital or operating room in which gloves are placed over the sleeves of a surgeon or other medical practitioner. Since such liquid repellant coatings are often expensive, such coatings may also add a significant expense to the costs of such garments. Finally, despite these additional coatings, medical personnel often use multiple layers of such nonwoven garments in order to create enhanced barrier protection (that is, they wear several gowns, one over the other). While such a practice may provide the desired barrier protection, such protection is almost always accompanied with a sacrifice in thermal comfort and range of motion.

Therefore, even with improvements in the disposable protective outerwear field, there continues to be a need for apparel with increased barrier protection, without a sacrifice in comfort.

Furthermore, despite the aforementioned improvements in materials, there continues to be breaches of the barriers while they are being used by medical service providers. The breaches can occur for many different reasons, such as a medical garment being caught on a medical instrument or device during a medical procedure, thereby creating a gap between pieces of clothing, or a medical garment actually being pierced during a medical procedure, or because liquid present in a medical setting may wick along a nonwoven material surface, or alternatively in conjunction with a glove line (that is the inside surface of a glove in contact with a nonwoven material surface) to a location on the medical service provider where there is either no or reduced barrier protection. For instance, as can be seen in FIG. 1, if a medical practitioner is exposed to large amounts of blood during a medical procedure, it is possible for blood to wick along a glove or booty (foot cover or foot protection) line as the case may be, that is adjacent and overlapping a nonwoven garment sleeve or leg, and eventually to the inside surface of the glove or shoe cover. For the purposes of this application, the term "outside surface" shall mean the surface of protective workwear facing away from a person wearing such workwear. The term "inside surface" shall mean the surface of protective workwear facing the body of the person wearing the protective workwear, i.e. closest to the skin of the person. The terms "protective workwear" and "protective outerwear" shall be used synonymously.

As can be seen in FIG. 1, a porcelain model of a medical provider's hand 10 has been donned with one surgical glove 20 (easily seen by the rolled up glove edge ridge or "beaded" edge). Prior to the donning of the glove, an exemplary sleeve of a medical gown 30 has been placed over the model's wrist, and lower arm area, with the sleeve including a cuff 32. The glove has then been placed over the model, and in an overlapping fashion, over the cuffed lower sleeve portion of the garment. Liquid 34 (in this case, 20% isopropyl alcohol and water with red food coloring for ease of visualization, (all with surface tension of approximately 32 dynes/cm, as a preliminary model for fluids that a medical provider may contact in a surgical theater) is shown to have wicked along the outside surface of the nonwoven garment, along the inside surface of the glove and up the inside surface of the nonwoven garment. Subsequently, the arm mold 10 became wet at various locations.

Of course, whether such liquid actually reaches the hand/limb of a medical service provider does depend on a number of factors, such as the practice of a medical service provider to double glove, (or double donning) that is the practice of medical providers to place two or more gloves or other coverings over their hands/limbs, the order of double gloving, that is whether one glove is placed under a medical garment and one glove is placed over a medical garment or whether two gloves are placed one on top of the other, each over the garment, the types of gloves utilized (for instance, the size of the wrist/arm portion, and the composition of the glove) and the tension that they apply to the arm of the user, the liquid that is exposed to the medical service provider, the garment utilized (for instance whether the garment has sleeves and how long such sleeves are, and the composition of the medical garment), the number of garments worn by the medical service provider (for example, two sleeves from two garments worn over the arm) and of course the medical service provider's safety practices in dealing with large volumes of blood and other liquids containing potential contaminants.

Therefore, there is a need for medical and other protective workwear/outerwear apparel which may assist in reducing the possibility of wicking of blood and other liquids along apparel surfaces and/or along the inside surface of protective gloves/boots/or other covering that may be used in conjunction with the protective workwear.

Drop on demand, continuous, valvejet and other forms of ink jet printing apparatus have been used for a period of time to apply inks to a variety of substrates. Generally, a drop on demand ink jet printing apparatus operates to discharge individual droplets of ink onto a substrate in a predetermined pattern to be printed. Ink jet printing is a non-impact and non-contact printing method in which an electronic signal controls and directs the droplets or stream of ink that can be deposited on a wide variety of substrates. Current ink jet printing technology involves forcing the ink drops through small nozzles by piezoelectric pressure, thermal ejection, or oscillation, and onto the surface of a material/medium. Ink jet printing is extremely versatile in terms of the variety of substrates that can be treated, as well as the print quality and the speed of operation that can be achieved. In addition, ink jet printing is digitally controllable. For these reasons, ink jet methodology has been widely adopted for industrial marking and labeling. In addition, ink jet printing methodology has also found widespread use in architectural and engineering design applications, medical imaging, office printing (of both text and graphics), geographical imaging systems (e.g., for seismic data analysis and mapping), signage, in display graphics (e.g., photographic reproduction, business and courtroom graphics, graphic arts), and the like. Finally, ink jet printing has now also been used to create an image on a variety of textile and nonwoven substrates. While such ink jet printers have been used to print on discrete areas, heretofore it has not been known to use such efficient technology, where jetting of phase change materials (such as hot melt wax inks) is possible, to provide enhanced wicking protection to workwear garments. It is to such an application and others that the present invention is directed.

SUMMARY OF THE INVENTION

Protective outerwear for covering a body portion includes an inside surface and an outside surface. The outside surface includes thereupon a printed blocking material in a continuous unbroken band, region, or combination of such, for blocking the wicking of low surface tension liquids at least on the outside surface of the outerwear.

In an alternative embodiment, the protective outerwear includes low surface tension liquid blocking material on the outside surface in multiple bands. In still a further alternative embodiment the protective outerwear includes low surface tension liquid blocking material on the outside surface in a region. In still a further alternative embodiment, the protective outerwear includes low surface tension liquid blocking material on the outside surface in at least a band and a region. In still a further alternative embodiment the protective outerwear includes low surface tension liquid blocking material on the outside surface in a band having a width between about ⅛ inch to 1 inch. In still a further alternative embodiment, the protective outerwear includes low surface tension liquid blocking material on the outside surface in a band having a width between about ⅛ inch to ½ inch.

A protective outerwear garment having an inside surface and an outside surface includes a body portion; a neck portion; two sleeves attached to the body, each sleeve having an inside surface and an outside surface, each sleeve including a lower edge for encircling a user's wrist and hand, an elbow region for containing a user's elbow, and an upper edge attached to the body portion. The sleeves include at least along their outside surfaces a printed blocking material in a continuous unbroken band, region, or combination of such, for blocking the wicking of low surface tension liquids on at least the outside surface of the outerwear.

DEFINITIONS

Figure 1:
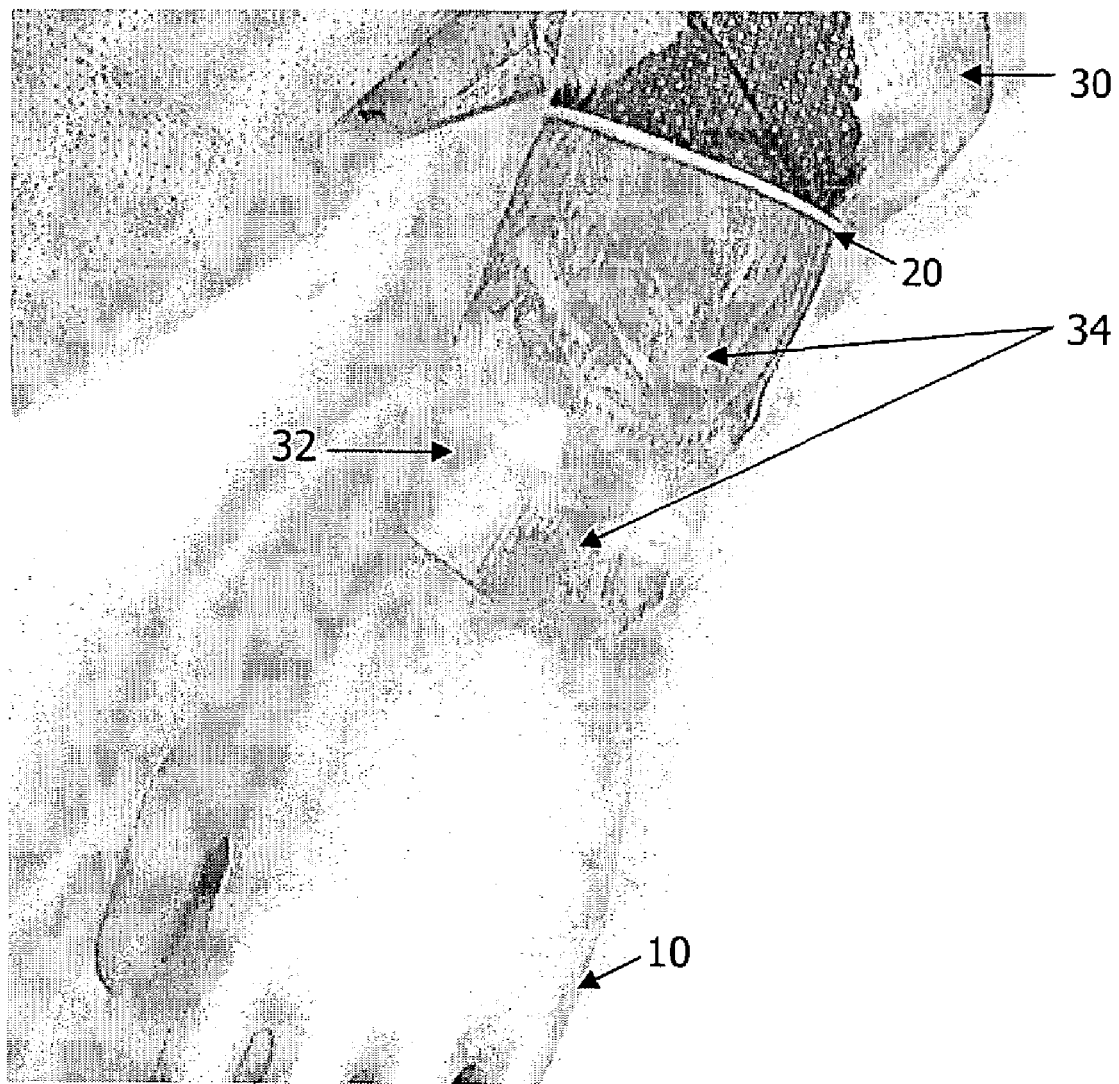
FIG. 1 illustrates a photographic image of a nonwoven fabric sleeve over a hand model and including a glove positioned over the model and sleeve edge.

As used herein the following terms have the specified meanings, unless the context demands a different meaning or a different meaning is expressed; also, the singular generally includes the plural, and the plural generally includes the singular unless otherwise indicated.

As used herein, the terms "comprises", "comprising" and other derivatives from the root term "comprise" are intended to be open-ended terms that specify the presence of any stated features, elements, integers, steps, or components, but do not preclude the presence or addition of one or more other features, elements, integers, steps, components, or groups thereof.

As used herein, the term "fabric" refers to all woven, knitted and nonwoven fibrous webs, unless one type is specified.

As used herein, the term "layer" when used in the singular can have the dual meaning of a single element or a plurality of elements.

As used herein the term "meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al., which is incorporated by reference herein in its entirety. Meltblown fibers are microfibers that may be continuous or discontinuous, are generally smaller than 10 microns in average diameter, and are generally tacky when deposited onto a collecting surface.

As used herein "multi-layer laminate" means a laminate wherein some of the layers are spunbond and some meltblown such as a spunbond/meltblown/spunbond (SMS) laminate and others as disclosed in U.S. Pat. No. 4,041,203 to Brock et al., U.S. Pat. No. 5,169,706 to Collier, et al., U.S. Pat. No. 5,145,727 to Potts et al., U.S. Pat. No. 5,178,931 to Perkins et al. and U.S. Pat. No. 5,188,885 to Timmons et al. each of which is incorporated by reference herein in its entirety. Such a laminate may be made by sequentially depositing onto a moving forming belt first a spunbond fabric layer, then a meltblown fabric layer and last another spunbond layer and then bonding the laminate in a manner described below. Alternatively, the fabric layers may be made individually, collected in rolls, and combined in a separate bonding step. Such fabrics usually have a basis weight of from about 0.1 to 12 osy (6 to 400 gsm), or more particularly from about 0.75 to about 3 osy. Multi-layer laminates may also have various numbers of meltblown (M) layers or multiple spunbond (S) layers in many different configurations and may include other materials like films (F) or coform materials, e.g. SMMS, SM, SFS, SMS etc.

As used herein, the term "phase-change" refers to a material which is processed at elevated temperatures in a liquid, substantially liquid or semi-solid state and then solidifies or returns to its natural state when cooled. The material or composition is desirably at least partially hydrophobic. The phase change liquid may be, for example, a wax, petrolatum based lotion, adhesive, thermoplastic, and so forth. As used herein, the term "petrolatum" refers to a semi-solid mixture of hydrocarbons obtained from petroleum, such as Glenpure L white petrolatum available from Glen Corporation of St. Paul, Minn.

The term "wax" shall mean a low-melting organic mixture or compound, which is thermoplastic but solid at room temperature and generally similar in composition to fats and oils. The term can include hydrocarbons, esters of fatty acids, and alcohols. Such materials are typically hydrophobic.

As used herein the terms "bonded" and "bonding" refer to the joining, adhering, connecting, attaching, or the like of two elements. Two elements will be considered to be bonded together when they are bonded directly to one another or indirectly to one another, such as when each is directly bonded to intermediate elements. Such bonding may occur for example, by adhesive, thermal or ultrasonic methods.

As used herein the term "thermal point bonding" involves passing a fabric or web of fibers to be bonded between a heated calender roll and an anvil roll. The calender roll is usually, though not always, patterned in some way so that the entire fabric is not bonded across its entire surface, and the anvil roll is usually flat. As a result, various patterns for calender rolls have been developed for functional as well as aesthetic reasons. One example of a pattern has points and is the Hansen Pennings or "H&P" pattern with about a 30% bond area with about 200 bonds/square inch as taught in U.S. Pat. No. 3,855,046 to Hansen and Pennings, incorporated herein by reference in its entirety. The H&P pattern has square point or pin bonding areas wherein each pin has a side dimension of 0.038 inches (0.965 mm), a spacing of 0.070 inches (1.778 mm) between pins, and a depth of bonding of 0.023 inches (0.584 mm). The resulting pattern has a bonded area of about 29.5%. Another typical point bonding pattern is the expanded Hansen Pennings or "EHP" bond pattern which produces a 15% bond area with a square pin having a side dimension of 0.037 inches (0.94 mm), a pin spacing of 0.097 inches (2.464 mm) and a depth of 0.039 inches (0.991 mm). Another typical point bonding pattern designated "714" has square pin bonding areas wherein each pin has a side dimension of 0.023 inches, a spacing of 0.062 inches (1.575 mm) between pins, and a depth of bonding of 0.033 inches (0.838 mm). The resulting pattern has a bonded area of about 15%. Yet another common pattern is the C-Star pattern which has a bond area of about 16.9%. The C-Star pattern has a cross-directional bar or "corduroy" design interrupted by shooting stars. Other common patterns include a diamond pattern with repeating and slightly offset diamonds with about a 16% bond area and a wire weave pattern looking as the name suggests, e.g. like a window screen, with about a 19% bond area. Typically, the percent bonding area varies from around 10% to around 30% of the area of the fabric laminate web. As is well known in the art, the spot bonding holds the laminate layers together as well as imparts integrity to each individual layer by bonding filaments and/or fibers within each layer.

As used herein, the term "ultrasonic bonding" or "ultrasonic welding" means a process performed, for example, by passing a fabric, such as a nonwoven material, between a sonic horn and anvil roll as illustrated in U.S. Pat. No. 4,374,888 to Bornslaeger, incorporated by reference herein in its entirety. When layers of fabric, or two or more fabrics, are ultrasonically bonded, the fabric(s) is/are respectively, heated to a melting point, such that all pores, capillaries, and so forth, if any, in the material collapse and/or are sealed in the melting process. The integrity and continuity of the material is maintained (i.e., the material does not become too thin or perforated in the bonded areas).

As used herein, the terms "nonwoven" and "nonwoven fabric" mean either a nonwoven web, scrim, netting, film, a foam sheet material, or a combination thereof.

As used herein the terms "fibrous nonwoven" and "fibrous nonwoven fabric or web" mean a web having a structure of individual fibers, filaments or threads which are interlaid, but not in an identifiable manner as in a knitted fabric. Fibrous nonwoven fabrics or webs have been formed from many processes such as for example, meltblowing processes, spunbonding processes, and bonded carded web processes. The basis weight of fibrous nonwoven fabrics is usually expressed in ounces of material per square yard (osy) or grams per square meter (gsm) and the fiber diameters useful are usually expressed in microns. (Note that to convert from osy to gsm, multiply osy by 33.91).

As used herein, the term "protective workwear" shall encompass medical garments or medical workwear and other forms of protective attire used by various industries/professions to protect workers from contaminants or to prevent the contamination of others. Such protective workwear includes but is not limited to hospital and surgical gowns, medical scrubs, medical drapes, coveralls, overalls, face masks, and garments used to protect either a portion of, or an entire body. For the purposes of this application, the terms "garment(s)" and "apparel" are used synonymously.

As used herein the term "spunbonded fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al. each of which are incorporated by reference herein in their entirety. Spunbond fibers are generally not tacky when they are deposited onto a collecting surface. Spunbond fibers are generally continuous and often have average diameters (from a sample of at least 10) larger than 7 microns, more particularly, between about 10 and 20 microns.

The term "low surface tension liquid" shall mean liquids that demonstrate a surface tension of between about 25 and 50 dynes/cm, but typically between about 30 and 45 dynes/cm. Surface tension may be measured in accordance with standard Wilhemy plate or tensiometer methods. Such low surface tension liquids include, but are not limited to scrub solutions, blood, isopropyl alcohol and other liquids that are commonly encountered during a medical procedure or in a medical environment.

The related term "hydrophobic" shall generally refer a nonwoven fabric that possesses a surface that does not promote the spreading of water. The water instead, forms drops and a contact angle that can be measured from the plane of the fiber/material surface, tangent to the water surface at the three-phase boundary line (air-water-fiber). Typically the contact angle is often greater than 90 degrees. Hydrophobic fabrics may be produced from materials that are inherently hydrophobic or from hydrophilic fibers/films that have been treated in some fashion to be hydrophobic. Such treatment may include chemical treatments.

The term "low surface tension liquid blocking material" is a substance that can be applied to a nonwoven material that will block the travel path of wicking low surface tension liquids. Such term shall include but not be limited to wax inclusive inks. It is used interchangeably with the term "circumambient material".

The term "wick" or "wicking" shall mean to carry moisture/liquid away, typically by capillary action. Such term also encompasses the ability of a liquid to travel between sheet materials, such as between the surface of a fibrous nonwoven sheet material such as a surgical drape and a film sheet, such as a glove.

The term "ink" shall mean any material, liquid or fluid that can be printed, or jetted from an ink jet printer. Inks shall include phase change liquids. Inks may be colored or uncolored.

The term "colored" shall mean containing a colorant or a coloring agent which is visually perceptible to the human eye. For the purposes of this application, such colorant may include pigments or dyes.

The term "uncolored" shall mean not containing a colorant or coloring agent which is visually perceptible to the human eye.

The term "contaminant" shall mean a chemical agent or biological organism/pathogen that can potentially harm a human being or animal.

These terms may be defined with additional language in the remaining portions of the specification.

DETAILED DESCRIPTION OF THE INVENTION

A structure has been developed to reduce the likelihood that low surface tension liquid such as blood will wick along the outside surfaces of a nonwoven material, and further, to reduce the likelihood that low surface tension liquids will wick between the outside surfaces of nonwoven materials of protective workwear and the inside surface of other coverings, such as gloves or boots/shoe covers worn over such workwear, so as to avoid the liquid traveling around or past the edges of such workwear to exposed areas of human skin. For example, such a structure will reduce the likelihood that blood will wick along the outside surface of surgical gowns and along the inside surface of gloves or foot coverings worn over such gowns.

Such a structure includes a nonwoven garment that has been treated to include a continuous line, band or path of low surface tension liquid blocking material deposited at least along an outside surface portion of a sleeve, leg, waist, or neck opening of such body garment. Similarly, such line, band, or path may be placed on a garment that goes on/or around the body extremities, such as on an ankle portion of a boot, hood portion of protective outerwear, side edges of facemasks, or wrist portions of hand coverings. Such blocking material is desirably situated adjacent the opening of such a garment. In the case of a sleeve, such blocking material is desirably at a location over which a glove will be placed during usage. For a leg, such blocking material is desirably at a location over which a booty or shoe cover will be placed during usage. For a shirt garment, such blocking material is desirably placed adjacent the waist portion (above the shirt tail), desirably above that portion of the garment that would be tucked in such that the continuous line of blocking material would not be gathered so as to break the continuity of the line or create overlapping of the fabric. For pants, such blocking material is desirably deposited below the gathered waist portion. If such blocking area would be gathered or overlapped it is possible that the continuous line of blocking material would be broken. In the unbroken state, such blocking treatment will act as a dam or gutter to prevent such low surface tension liquid from approaching the edges of a garment that surround a wearer's body part.

Alternatively such structure includes a nonwoven garment that has been treated to include a continuous region or area of low surface tension liquid blocking material deposited along at least an outer surface portion of a sleeve, leg, waist, or neck portion of such a garment. Such region is visually more than a printed line, and can be described as a generally wider area of blocking material application. In the case of a region, such a low surface tension liquid blocking material is placed in sufficiently wide a region/area to provide a continuous region that blocks the wicking of low surface tension liquids. However, such region does not encompass an entire arm, leg, neck or waist area, as such would potentially interfere with the comfort of the garment containing the treatment, and would unnecessarily add to the cost of such garments.

By "treated" and "treatment" is meant, exposed to, and brought in contact with a low surface tension liquid blocking material substance via one of numerous methods including but not limited to, application methods such as spraying, printing, dipping, or extruding. Such continuous lines, bands, paths or region/areas (or combination thereof) are desirably in the form of a line or ribbon of low surface tension liquid blocking material which circumscribes the outer surface of the sleeve, leg, waist, or neck portion of a garment. Such, line, band, path or region/area may comprise one or more linear or nonlinear bands, which sufficiently seal and/or block the pores, if any, of the garment in the treated line or region, at least along the outside surface of the garment, but desirably through the entire thickness of one or more of the layers of the garment. Such treated areas may include areas of continuous patterns and also include in some embodiments, discontinuous patterns, lines, bands or regions in addition to the continuous patterns, lines, bands or regions.

Desirably, such treated lines, bands or areas on the workwear are immediately adjacent an untreated line, band or area, so as to provide contact areas of varying coefficients of friction, should a glove or shoe cover be placed over such workwear areas. In this fashion, the glove or shoe cover is less likely to slide during use, as the varying coefficients of friction provide degrees of traction to maintain the glove/shoe cover or other covering in position. In some instances, it may also be desirable for such untreated areas adjacent the blocking materials to demonstrate some level of surface absorption (in a garment with at least one inner barrier layer), and serve to hold the low surface tension liquid within a defined outer layer of the garment and in an area adjacent the low surface tension liquid blocking material.

In the case of a hospital or surgical gown, such treatment of circumambient material is desirable situated on each arm, between the cuff region and the elbow region of a gown. Such a medical gown desirably includes a body covering portion and sleeves extending from the body portion that end in sleeve ends or in cuffs. Such circumambient material is desirably equidistant from the cuff or sleeve/leg/waist edge of the protective workwear (that is the edge of the garment opening surround the limb), but is not required to be so situated. Further, such circumambient material desirably penetrates/and blocks the pores of a nonwoven garment (if any) so as to create a barrier line through the entire thickness of the garment, thereby functioning as a gutter to collect/stop or dam the low surface tension liquid from proceeding past the circumambient material and into the cuff or sleeve edge region, or ankle region as the case may be. If the gown is of a multiple layered fabric with a barrier layer between an inside surface and an outside surface, it is desirable in one embodiment to have the treatment penetrate the thickness of the outside surface layer.

In an alternative embodiment, such circumambient material may be deposited in a nonuniform thickness application, such that a thicker, heavier deposit could be placed in areas of high contact, or wider areas of circumambient material can be placed in such locations.

While, such circumambient material may be deposited in a continuous straight line or path around the garment, it is not necessary that such be the case. For instance, such material may be deposited in a loop pattern or some other regular or irregular pattern around the garment circumference, so long as it is continuous, without any breaks or gaps. For instance, an artistic pattern may be employed in order to make the garment more aesthetically pleasing or to improve brand name recognition.

In the case of protective medical garments, such low surface tension liquid blocking material desirably is positioned at a location on a sleeve that will be covered by a glove, when a glove is positioned over such sleeve during the medical service provider's preparatory dressing. By allowing the circumambient material to be present only in the forms of narrow bands or regions, a gown treated in such a fashion, provides for a gutter to block the spread of wicking liquid, but also allows for the frictional contact of the gown sleeve and a glove, thereby allowing the glove to remain securely positioned over the gown. Further, such strategic placement of circumambient material, is cost efficient, thereby leading to a lower cost garments.

Also, by treating garments in this fashion, discrete lines of demarcation may become evident on the sleeve, leg or other treated portion which separates a portion of a sleeve that has been exposed to a low surface tension liquid, and a portion of a sleeve which has not. As a result of such treatment, the occurrence of liquid wicking up the interior layer of the nonwoven garment (for instance, the layer/inside of the garment in contact with the medical service provider's arm) will likely be reduced. Additionally, the low surface tension liquid will likely be maintained on the outside surface of the garment.

Figure 2:
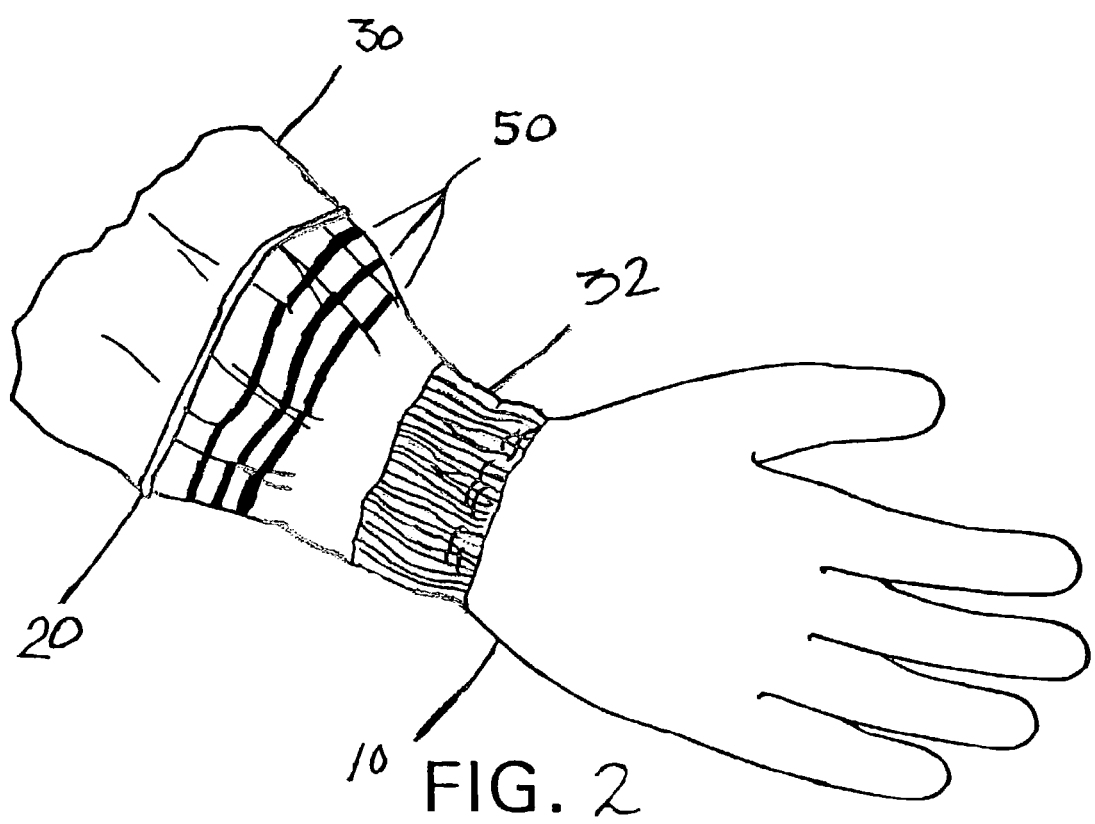
FIG. 2 illustrates a perspective view of an alternate embodiment of a nonwoven sleeve in accordance with the invention which includes multiple continuous colored bands of low surface tension liquid blocking material deposited along a sleeve surface.

In FIG. 2, an embodiment of such a treated garment is illustrated. In this embodiment, a series of colored bands 50 surround the garment sleeve, thereby creating a multiple stepped barrier to low surface tension liquids. An untreated area on the garment is situated between each of the bands. While the bands are shown as seen through the glove 20, it is not necessary that they be so.

Figure 3:
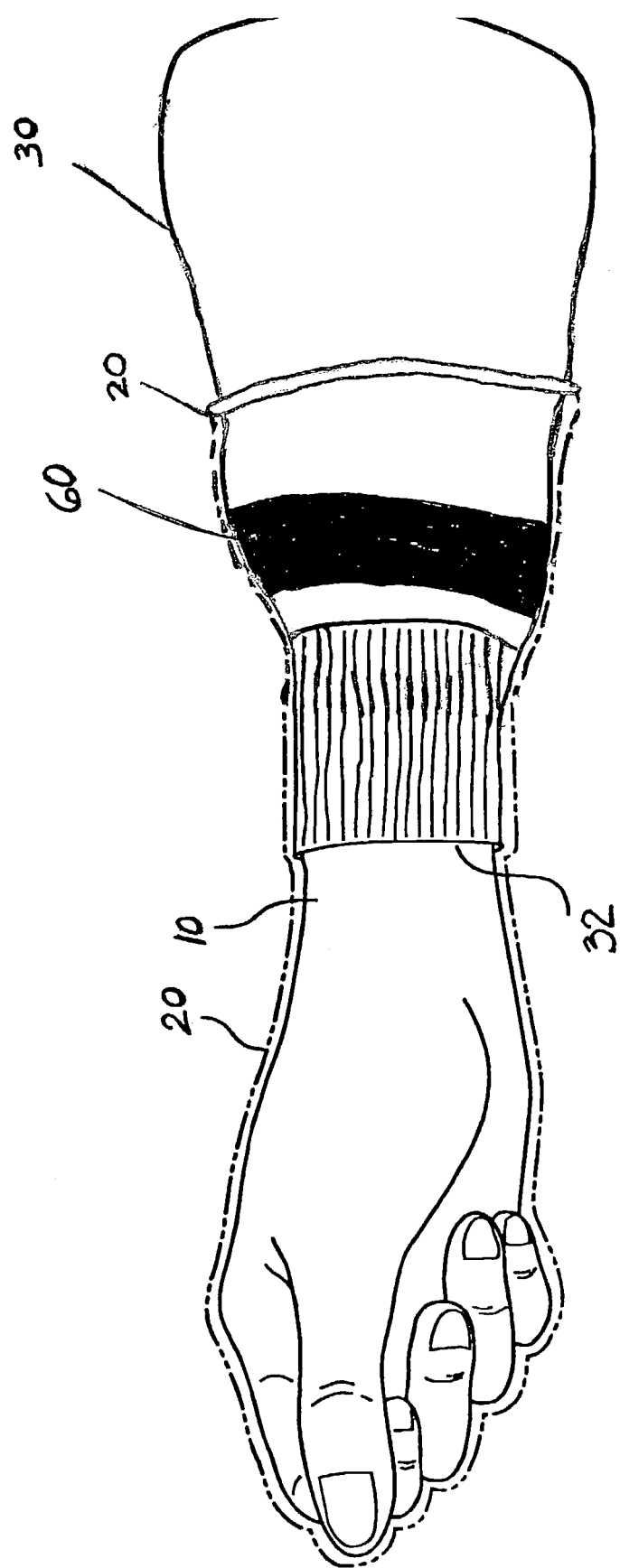
FIG. 3 illustrates a perspective view of an alternate embodiment of a nonwoven sleeve in accordance with the invention which includes a continuous colored area of low surface tension liquid blocking material deposited along a sleeve surface.

In FIG. 3, a further alternate embodiment of the treated garment of FIG. 2 is illustrated. In this embodiment, a colored continuous region/area 60 surrounds the garment sleeve and is adjacent untreated areas. This region is also shown as visible through the glove 20.

Figure 4:
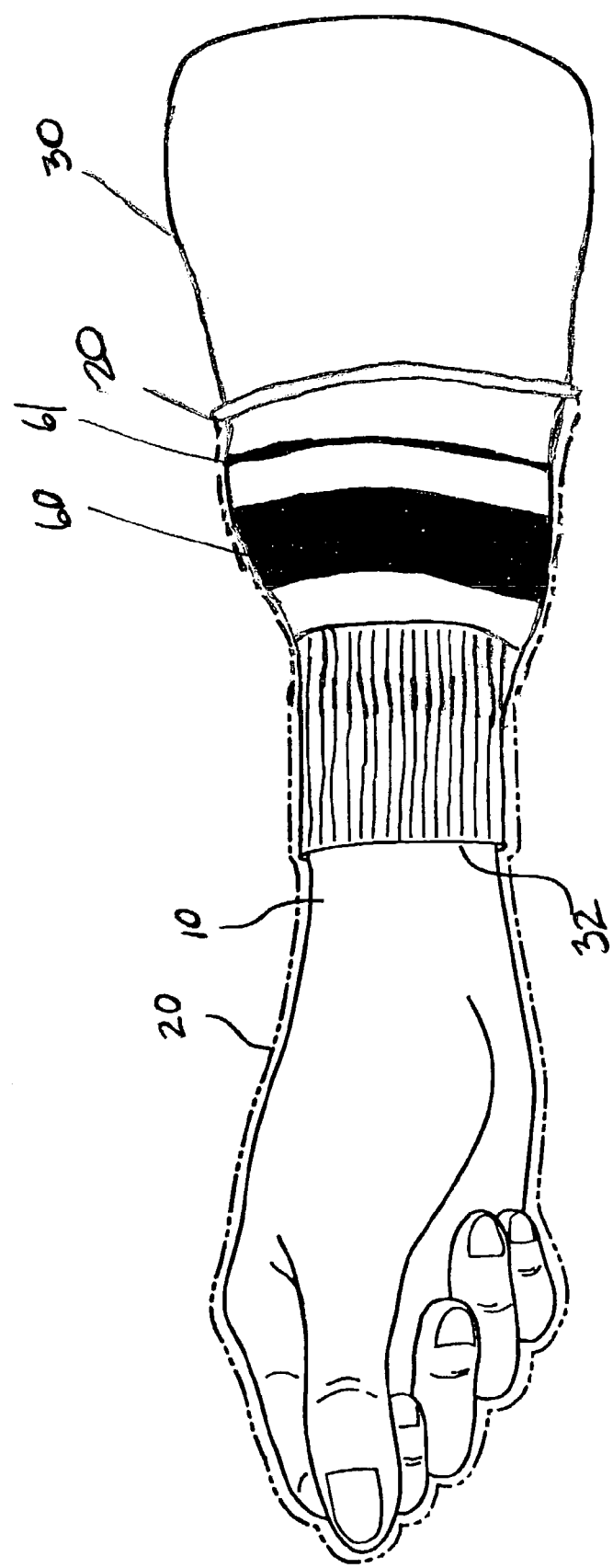
FIG. 4 illustrates a perspective view of an alternate embodiment of a nonwoven sleeve in accordance with the invention which includes a combination of a continuous colored area of low surface tension liquid blocking material deposited along a sleeve surface and a continuous colored band of low surface tension liquid blocking material deposited along a sleeve surface.

In FIG. 4, still a further alternate embodiment of the treated garment of FIG. 2 is illustrated. In this embodiment, a colored continuous area 60 surrounds the garment sleeve. This continuous area is adjacent a single band of colored material 61, with the continuous area and single band each creating a barrier to low surface tension liquids, and separated by an untreated area. As in the previous figures, the region and band are both shown as visible through the glove 20.

Such low surface tension liquid blocking material lines, bands or paths (deposits), are each desirably between about ⅛ to about 1 inch in width and are positioned in a continuous generally linear path around the circumference of the sleeve, leg, waist, or neck opening, desirably equidistant from the garment opening. More desirably, such blocking material, lines, bands, or paths have a width between about 3/16 and about 1/2 inch. If a low surface tension liquid blocking material is present either by itself, or in conjunction with additional blocking aids (such as bonds which are described below), it is desirable that such additional blocking aids have a width of between about 1/4 and 1/2 inch in width. As previously indicated, it is desirable that such low surface tension liquid blocking materials not occupy the entire area of a limb, neck or abdominal portion of a garment, as such will have a negative impact on the comfort of a garment (limiting the ability of perspired moisture to leave the garment), would appreciably add to the costs of a garment, and could negatively impact the ability of a glove or foot covering to stay situated over the garment as a result of low coefficients of friction (thereby leading to sliding of the glove along the garment during use). It therefore is desirable for an area of separation to be between regions or bands of blocking materials of between about 1/2 inch and 2 inches in width in order to maintain a high coefficient of friction between gloves or shoe coverings and gowns. More desirably, there is an area of separation between regions or bands of blocking materials of about 1 inch width.

For the purposes of this application, the term "continuous region" shall be used to describe an area of the workwear having a low surface tension liquid blocking material deposited thereon having at least 1/8 inch width. For the purposes of this application the terms "line(s)", "path(s)", "band(s)" and/or "pattern(s)", shall refer to a continuous region around the garment sleeve, leg or opening, that is less than 1 inch width. Desirably, a band is present on a sleeve of a gown approximately between about 1/2 inch and about 6 inches from the edge of the gown cuff or sleeve edge surrounding the wrist of the user.

In still a further alternative embodiment of the present invention, the garment may include in addition to the previously described low surface tension liquid blocking material deposits, outwardly turned up edge portions at the edge of the sleeve, leg, pant, waist or other garment portion edge/margin (surrounding the body portion) so as to create a further dam-like/pocket structure. Still in a further alternative embodiment, such treated garment may include additional barrier aids, such as thermal or ultrasonic bonds along the garment edge portions, to further seal the garment from wicking fluids. In such embodiments, the garment would be bonded sufficiently to close/seal any pores in at least an outer layer, but not so bonded as to create perforations, or weaknesses in the garment structure. Such bonding would through bonding means, achieve a blocking of low surface tension liquids, that could supplement the blocking means provided by treating the garment topically with a chemical application (inks serving as low surface tension liquid blocking material deposits). Still in another alternative embodiment of the present invention, a garment that has been so treated, may include traditional cuffs that have been added to edges of the sleeves, or cuff-like structures that have been added to the edges of the legs, waist or neck portions and that have been further treated in some fashion so as to repel certain liquids.

Figure 10A:
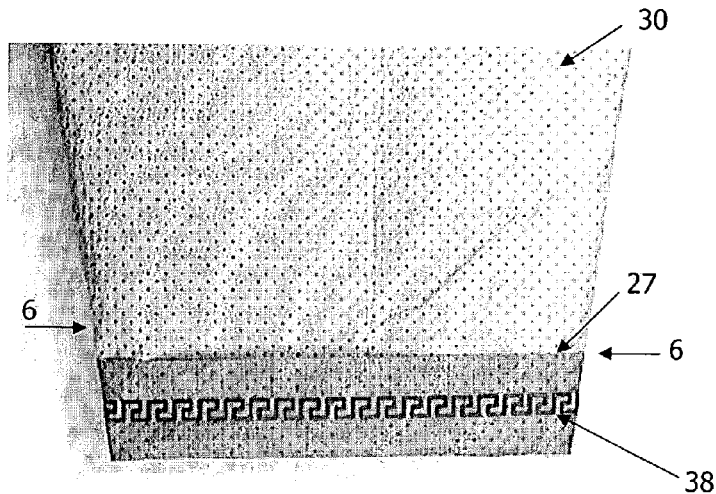
FIGS. 10A–10C illustrate a photographic image of an alternate embodiment of a nonwoven sleeve constructed in accordance with the present invention in which a lower end of the sleeve has been turned upward, and in which a plurality of continuous ultrasonic bonded bands, the bands having a pattern, are positioned circumferentially about a sleeve surface.
Figure 10B:
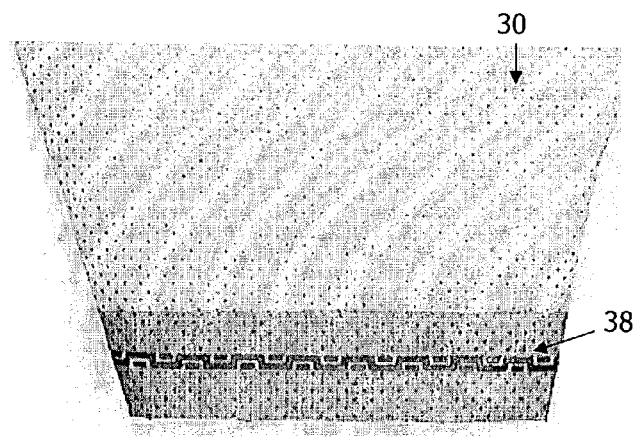
Figure 10C:
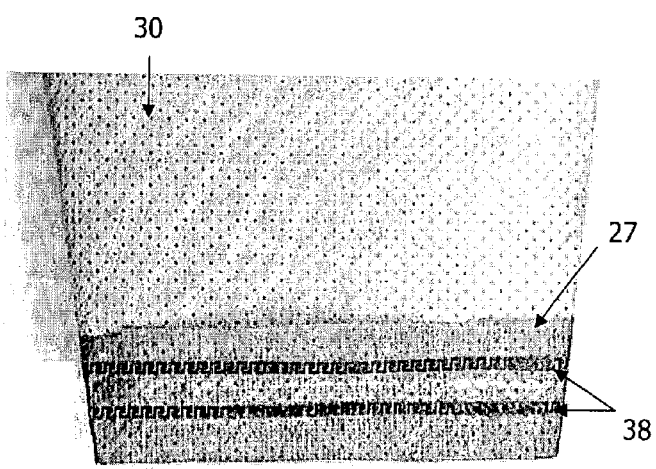

For instance, in FIGS. 10A–10C, aspects of these alternate embodiments are illustrated. In particular, upturned sleeve edges and bonded portions are photographically illustrated. The garment may include in addition to the previously described treatments, outwardly upturned end sleeve portions 27 on the edge of the sleeve 30 with ultrasonic bonded barriers 38 and may also include, by way of non-limiting example, a leg edge, a neck edge and/or a waist edge that have been hemmed ultrasonically (not shown). Such upturned portions provide yet another structural barrier to the spread of wicking low surface tension liquids. A cuff, of the type previously described herein could then be attached to the sleeve at the hemmed area or sleeve edge. In FIG. 10A, a single ultrasonically bonded barrier 38 in the form of a patterned band surrounds an upturned garment sleeve. The patterned band provides both a low surface tension liquid blocking functionality (since it closed the pores on the outside surface) as well as a bond between the layers of the garment sleeve 30, if any. This band or pattern 38 provides both a gutter and a holding area or pocket (illustrated as 48 in FIG. 11) for retaining low surface tension liquid. In FIG. 10B, an alternative embodiment similar to that shown in 10A is illustrated, except that the patterned band 38 has a different pattern. In FIG. 10C, an alternative embodiment of the treated garment sleeve 30 is also illustrated. In this embodiment, a pair of bonded continuous bands 38 which surround an upturned garment sleeve 30 are illustrated. The pair of bands 38 provides both low surface tension liquid blocking functionality as well as a pair of bonds between the layers of the garment sleeve 30. The bands provide gutters and pockets (48 in FIG. 11) for retaining low surface tension liquid to be contained on an outer surface on either side of the bands.

Figure 11:
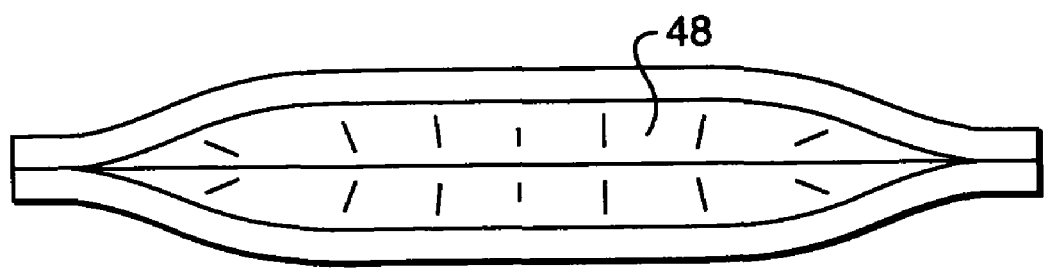
FIG. 11 is a sectional view of FIG. 10A taken along lines 38.

FIG. 11 is a sectional view of FIG. 10A taken along line 38, illustrating a pocket 48 which is formed when one or more layers of the garment sleeve 30 are thermally or ultrasonically bonded to each other to provide one or more continuous bands, namely, but not by way of limitation, lines, paths, patterns, regions, and so forth of low surface tension liquid blocking functionality but not depending on material deposition, as is illustrated generally in FIGS. 10A–10C.

Such bonding may be accomplished via a vibrational ultrasonic sewing machine. Vibrational ultrasonic sewing machines are commercially available, and one such ultrasonic sewing machine, Model LM 1220 manufactured by Sonobond Ultrasonics, West Chester, Pa., was used to create the bond patterns illustrated in FIGS. 10A–10C. The useful range of frequencies is very wide. Frequencies of up to about 40 kHz and about 20 kHz are often used commercially. However, frequencies of, for example, 18 kHz and as low as 10 kHz have also been used in some applications. The power settings used commercially are often in a range of 10 Watts to 1000 Watts, although other power settings may be utilized. Desirably, the power settings are in a range of about 50 Watts to about 900 Watts; more desirably, the power settings are in a range of about 100 Watts to about 500 Watts.

Desirably, the pressure settings for both the ultrasonic horn and the pattern wheel are set in a range of about 1 psi to about 100 psi. More desirably, the pressure settings for both the ultrasonic horn and the pattern wheel are in a range of about 5 psi to about 50 psi. More desirably, the pressure settings for both the ultrasonic horn and the pattern wheel are in a range of about 10 psi to about 40 psi.

The particular "pattern" used for the pattern wheel determines the width and pattern for the low surface tension liquid blocking bond. Height and spacing of projections on the pattern wheel will be selected in accordance with the desired end product. For example, the height will preferably be approximately the thickness of the formed web of the garment, and the projections and/or pattern will preferably be continuous and sufficient to provide substantial lamination of the formed web, through all layers thereof.

The ultrasonic horn and the pattern wheel are each adjustable for varying speeds. Desirably, the horn and wheel are both set speeds in a range of about 1 foot per minute to about 100 feet per minute. More desirably, the horn and wheel are set at a speed of about 2 to about 60 feet per minute. Even more desirably, the horn and wheel are set at speeds of about 6 to about 40 feet per minute. When two similar materials are positioned in the nip between the ultrasonic horn and the pattern wheel, it is desirable to have the same speeds for both. When two different materials are positioned in the nip, for example, a textured material adjacent the ultrasonic horn and a non-textured material adjacent the pattern wheel, the speed of the wheel may need to be somewhat faster than the speed of the ultrasonic horn, due to the frictional differences between the textured and non-textured materials.

Heat or thermal sealing and bonding of materials are well known in the art, and various thermal bonding equipment is discussed herein. One such piece of equipment utilized with the present invention is a Vertrod Thermal Impulse Heat Sealer, available from Therm-O-Seal, Mansfield, Tex. The useful range of heat settings and speeds are very wide. However, heat settings creating a degree of melting of a nonwoven material without interfering with the integrity and continuity of the material, i.e., causing thinning, slitting or perforations, are generally accepted as optimal, and are commercially used. Such heat settings are desirably between about 150 degrees F. to about 400 degrees F. (about 66 degrees C. to about 205 degrees C.) More desirably, the heat settings are about 280 degrees F. to about 320 degrees F. (about 138 degrees C. to about 160 degrees C.). Speed settings for heat sealing or bonding nonwoven materials are desirably in a range of 1 foot per minute to about 60 feet per minute, although thermal sealing may be accomplished by hand at lower and/or varying speeds. It will be appreciated that the heat settings used will be adapted to the particular characteristics of the material; the speed used will be adapted to the length, curves, and so forth of the material as well. As noted previously herein, rollers and so forth may provide a linear seam or bond; continuous pattern(s) may be provided as well. As discussed above the continuous pattern may be supplemented with a discontinuous pattern, if desired.

While numerous application methods may be used to apply the low surface tension liquid blocking material to a garment, desirably, printing, and particularly ink jet printing technology is used to apply a band, region or combination of such low surface tension liquid blocking material to the protective workwear sleeve, leg, neck, abdominal or torso regions. Such inks may be printed onto the nonwoven fabric substrates using a variety of ink jet printer technologies, such as drop on demand, continuous, valve jet and other ink jet printers.

In particular, ink jet printing technology can be used to apply discrete continuous areas of phase change inks (desirably hot melt wax inks) to these portions of the protective workwear garments. For example, in practicing the invention, a continuous band of colored or uncolored wax-based ink is applied around the periphery of a sleeve or other desired portion of a garment or garment material prior to garment manufacture. Desirably, such band is applied in a fashion that it clogs and coats the pore structure of the nonwoven fabric and thereby prevents liquid from wicking past the treated region at all thickness levels of the garment. In an alternative embodiment, the treatment is applied in a fashion such that it clogs and coats the pores of an outside surface layer of a garment. This method leaves a modified region on the garment that is, if the ink is colored, visibly apparent prior to being used, and if the color is not present, becomes visibly apparent upon soiling of the garment with a low surface tension liquid, as the stain of soiling would stop at a distinct line along the outside surface of the garment. In this fashion, the worker, or medical service provider receives a visual cue if the ink is colored, as to how far to pull up their gloves to obtain maximum protection. For instance, it would be desirable to pull the wrist portion of a glove, or the ankle portion of a shoe cover so that it overlaps the treated region of the garment. If the ink is not colored, then the presence of the line of demarcation (that is the separation of a stained area from an unstained area) will also serve as a visual cue that soiling has occurred and the medical service provider may want to initiate a change of clothing/gloves.

Ink jet printing technology provides an efficient method of applying wax containing ink and other chemistries to nonwoven fabrics, in discrete patterns. By digitally finishing nonwoven garments in this fashion, graphics can be generated with pattern features on a micron scale. Such webs may be treated at rapid production speeds to make such treatment methods cost effective, and at sufficient volumes to allow for the level of depth penetration required by the application.

In particular, it has been found that application of inks containing waxes and/or lotions to nonwoven materials with the inks having melting points of between about 70 and 140° C. can be applied to nonwoven materials in various patterns to successfully block the wicking of low surface tension liquids, and without damaging the structural integrity of the nonwoven garment. The exact melting points desired however, are dependent on the melting points of the polymeric materials making up the nonwoven garments.

The low surface tension liquid blocking material (such as a hot melt wax-ink or other phase-change liquid) may be applied to the garment fabric or garment outside surface by various ink jet printing techniques. For example, the low surface tension liquid blocking material may be deposited by use of a piezo-driven print head. The piezo-driven print devices are typically capable of emitting droplets having a diameter in the range of about 50–90 micrometers with placement resolution to about $\frac{1}{200}$ of an inch. The blocking material may be deposited in a single or multiple pass of the garment fabric or other layer, past the print head, or under the printhead as a single set of streams (if such is a part of the machine direction manufacturing process). In an alternate desirable embodiment, the liquid blocking material is deposited by a continuous inkjet printing technique.

Figure 8:
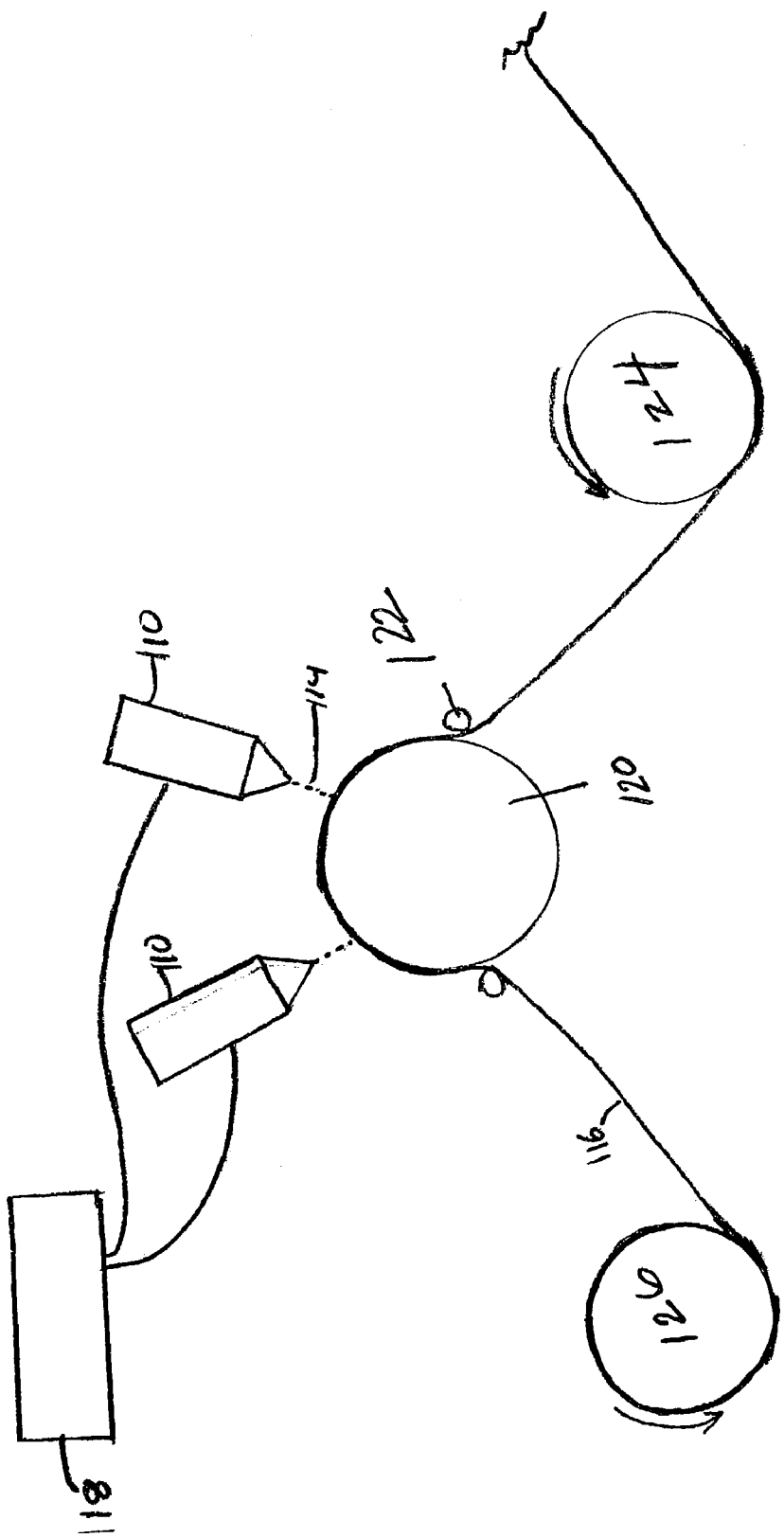
FIG. 8 is a schematic view of a drop on demand (piezo) ink jet printing system for printing on protective outerwear apparel.
Figure 9:
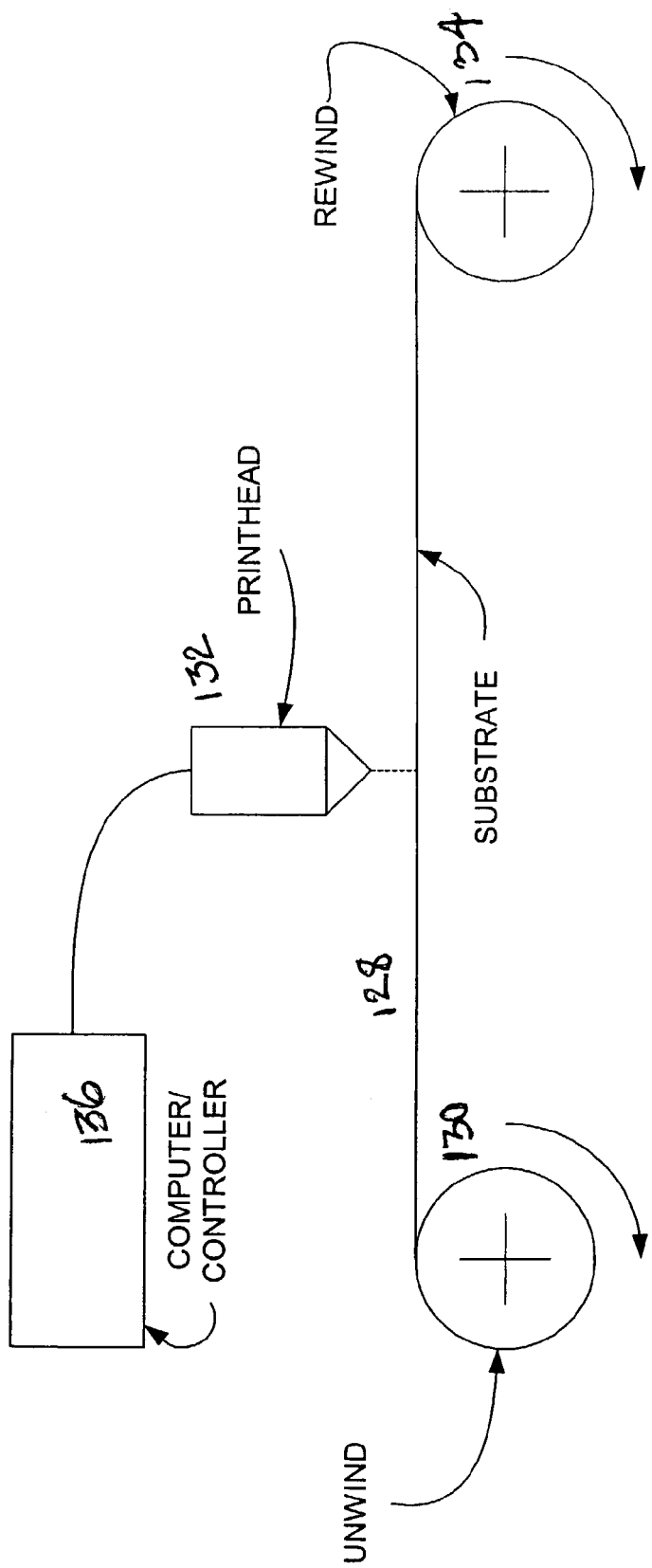
FIG. 9 is a schematic view of a continuous ink jet printing system for printing on protective outerwear apparel.

For the purposes of illustrating various ink jet application methods, FIGS. 8 and 9 have been provided. FIG. 8 illustrates a method of creating multi-color process images at high speed. The method includes providing at least two high-operating frequency printheads 110 which are capable of processing phase change inks (hot melt inks), providing at least two phase change inks 114, providing a substrate 116, activating the printheads such that at least two inks pass therethrough, and passing the substrate 116 under the printheads at a rate desirably between about 100 to 3000 feet per minute, wherein at least one process image, such as a continuous line or pattern is formed on the substrate 116. For instance, utilizing this method, stripes (bands) or other patterned prints can be deposited along the surface of the layer or product. In one embodiment of the method of the present invention the printheads may have operating frequencies of at least about 20 kHz. Any suitable printhead may be used provided it is capable of performing at the frequencies identified with any one or more of the inks discussed herein. As previously indicated, it is desirable for the inks to be hot melt phase change inks, and in some instances more desirable for the phase change inks to be wax based. While reference is made to passing, conveying or otherwise transporting the substrate or material under the printhead, the same terminology is also intended to include passing the printhead over the substrate or the combined movement of the printhead and the substrate such that the desired production speeds may be achieved.

The use of phase change inks, and specifically hot melt inks, and more specifically hot melt wax based inks, enables the high speed printing desired herein as the phase change inks do not require any additional significant drying step. Previously, the drying time of inks and compositions used in printers limited production speeds. The use of phase change inks eliminates the need for additional drying steps and/or space between the printheads (for different color applications) which was previously necessary. Thus design registration and image quality may be achieved if desired, without sacrificing high production speeds. In a further embodiment of a print method for manufacturing materials of the invention, a controller or other control means 118 may be provided that is in communication with the printheads. The control means 118 is desirably capable of operating in multiple modes and may control the printheads 110 such that the printheads 110 act together or independently from one another. It will be appreciated that any number of control means are suitable for use with the present invention depending in part on the number of printheads each control means is in communication with. Exemplary control means may vary from manual to computer controlled or computer regulated control elements (e.g. manual switches, line driven switches, photo-optic sensors, and software driven switching circuits).

As illustrated in FIG. 8, part of the substrate transport system is a drum 120 and a plurality of idlers 122. The drum and idlers 122 are designed to be compatible with the substrate material 116 which is passing over them such that the substrate 116 is in a substantially wrinkle free condition as it passes over or around the drum 120. The idlers 122 may be adjusted such that a desired level of tension may be applied to the substrate material 116 to eliminate or reduce the wrinkles that otherwise might be present in the material 116 were it to pass over the drum 120 without having some tension force applied thereto. That is, the idlers, 122 may be used to create or maintain a desired tension on the material 116 as it passes over the drum 120. It should be appreciated and understood that while a drum 120 is shown in FIG. 8, the present application is not intended to be limited thereto. Any number of drums or idler combinations may be used. Further, while the spacing between the printheads and the substrate to be printed may vary, it is desirable for the material 116 to be about 2 to 3 mm from the printhead when the ejection of ink occurs. Following printing, the material that has been fed to the drum from feeder roll 124, is then wound about winder roll 126.

In an alternative embodiment of a print method, as shown in FIG. 9, a substrate 128 to be printed is unwound from a feeder roll 130 and passed under a printhead of a continuous printer 132 that is then rewound on a winder roll 134. As in the previously described ink jet printer system arrangement, a computer controller 136 controls the printhead 132. While the substrate is illustrated as passing between two rolls, it can also travel along a forming wire or continuous belt, depending on manufacturing preferences.

The phase-change liquid is desirably applied at high add-on levels in thin bands. The add-on level in the treated area(s) is desirably between about 10 gsm (grams per square meter) to about 500 gsm, desirably less than about 400 gsm, and more desirably between about 100 gsm to about 300 gsm in the treated areas.

As previously indicated, such phase change liquids (i.e. wax inclusive inks) should be selected such that their application through an ink jet printer is not under conditions that would cause significant damage to the underlying layer (substrate material) to be printed. For instance, the application and application conditions of such inks should be such that they do not rupture either by force or by heating, the layer on which they are being printed. Generally, such hot melt waxes that are applicable for practice of this invention should have melting points lower than that of the material layer on which they are being printed.

Such wax inclusive inks should be non-allergenic and the contact of such inks to the skin of a user should not cause any noticeable irritations. Further such inks should adhere to the various layers to which they are applied and maintain their integrity and position during use of the product.

A wide variety of inks may be used as low surface tension liquid blocking materials for the nonwoven fabric substrates of the invention. Such inks include but are not limited to, hot-melt ink jet ink formulations such as those available from Spectra, Inc. of Hanover, N.H., under the brand names SABLE, and SABRE, ink formulations available from Tektronix, and those available from Westvaco. Examples of such inks are also described on pages 198–201 of Ink Jet technology and Product Development Strategies, by Stephen F. Pond, copyright 2000, of Torrey Pines Research, which pages are incorporated by reference herein.

As previously indicated, such low surface tension liquid blocking treatments may be utilized with a variety of nonwoven fabrics. Desirably, such treatments are used on nonwoven materials as described in U.S. Pat. Nos. 4,535,481, 5,213,881, 5,271,883, 5,464,688, 5,695,868, 5,855,999, 6,037,281, each of which is hereby incorporated by reference in its entirety. Such materials include fibrous nonwoven laminate materials such as spunbond-meltblown-spunbond fibrous materials and film-fiber laminate materials. Typically such materials have been produced by known nonwoven manufacturing processes that include bonding of the layers, such as thermal point bonding.

Figure 6:
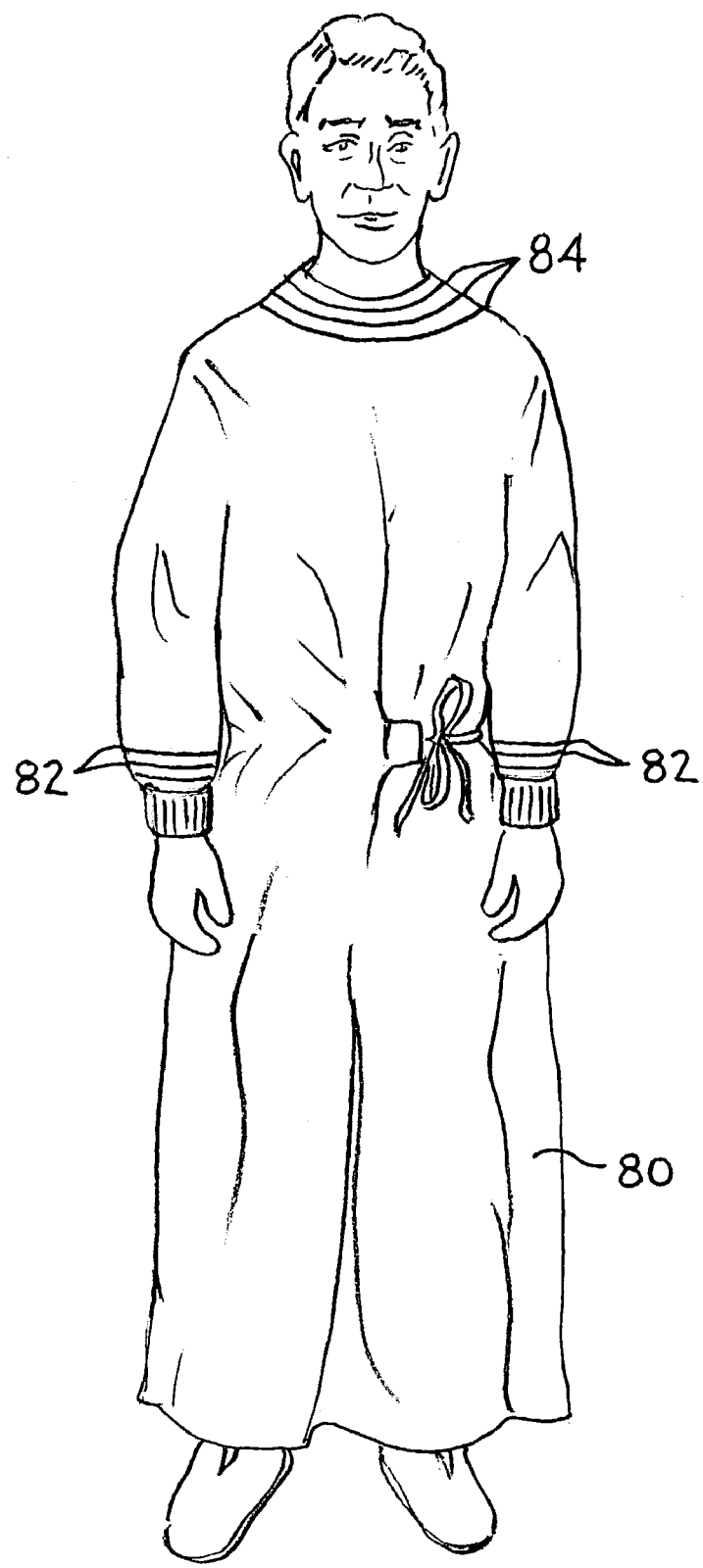
FIG. 6 illustrates an exemplary protective garment in accordance with the invention, namely a surgeon's gown.
Figure 7:
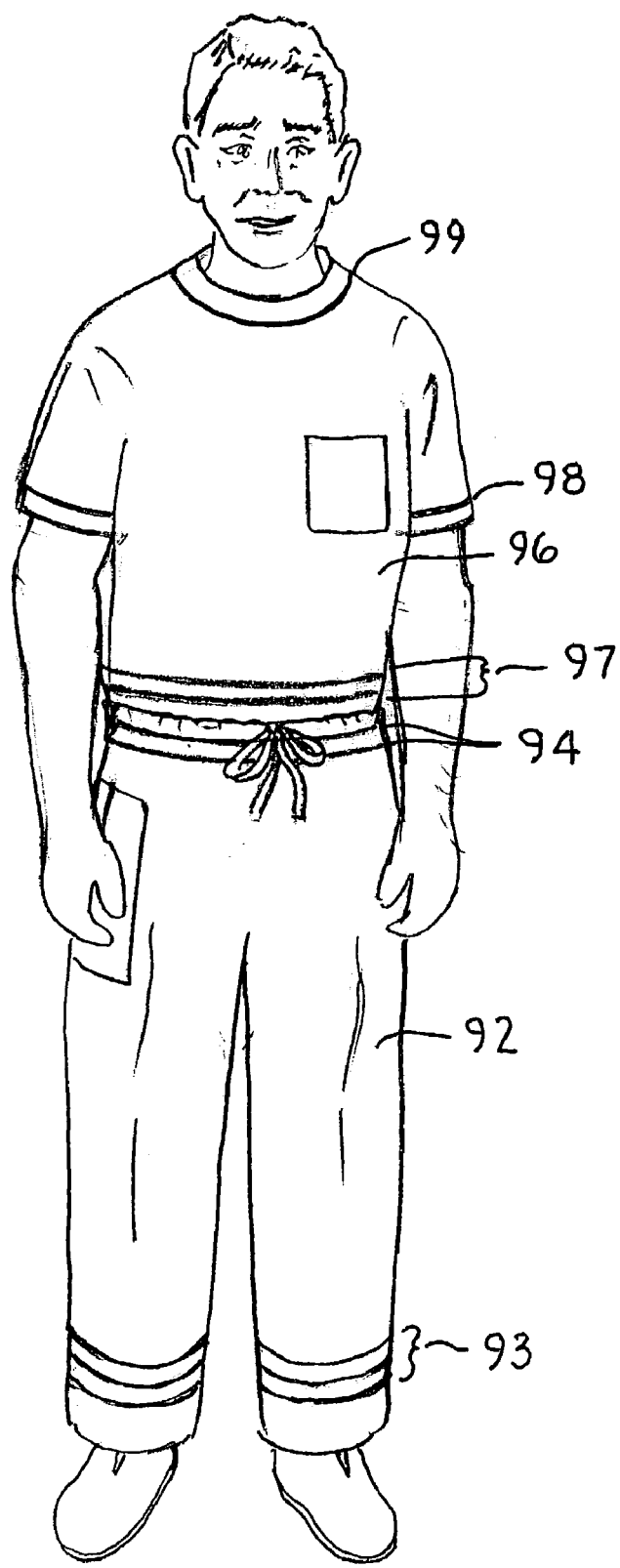
FIG. 7 illustrates another exemplary protective garment in accordance with the invention, namely medical scrubs.

As illustrated in FIGS. 6 and 7, a wide variety of protective workwear may be treated with low surface tension liquid blocking material as previously described. For the purposes of example only, as can be seen in FIG. 6, a surgical gown 80 has been treated with such blocking material in a multiple band configuration at the sleeve areas 82, and the neck areas 84. As can be seen in FIG. 7, a medical scrub set, consisting of a pant garment 92 and a shirt garment 96, has been treated with either a single or multiple band treatment at the leg ankle areas 93, waist area 94, shirt tail area 97, arm areas 98, and neck area 99.

The present invention is desirably used with an improved cloth-like, liquid-impervious, breathable barrier material, such as that disclosed in U.S. Pat. No. 6,037,281, which is incorporated in its entirety by reference herein, and which is discussed below. The breathable barrier material possesses a unique balance of performance characteristics and features making the material suitable for use in forming surgical articles, as well as other garment and over-garment applications, such as personal protective equipment applications. The barrier material is a laminate comprising three layers—a top nonwoven layer formed, for example, of spunbond filaments, a bottom nonwoven layer formed, for example, of spunbond filaments, and a middle breathable film layer formed, for example, of a microporous film. The individual layers of barrier material are laminated, bonded or attached together by known means, including thermal-mechanical bonding, ultrasonic bonding, adhesives, and the like. As used herein, the terms "layer" or "web" when used in the singular can have the dual meaning of a single element or a plurality of elements.

Commercially available thermoplastic polymeric materials can be advantageously employed in making the fibers or filaments from which the top and bottom layers are formed. As used herein, the term "polymer" shall include, but is not limited to, homopolymer, copolymers, such as, for example, block, graft, random and alternating copolymers, terpolymers, etc., and blends and modifications thereof. Moreover, unless otherwise specifically limited, the term "polymer" shall include all possible geometric configurations of the material, including, without limitation, isotactic, syndiotactic, random and atactic symmetries. As used herein, the terms "thermoplastic polymer" or "thermoplastic polymeric material" refer to a long-chain polymer that softens when exposed to heat and returns to the solid state when cooled to ambient temperature. Exemplary thermoplastic materials include, without limitation, polyvinyl chlorides, polyesters, polyamides, polyfluorocarbons, poly-olefins, polyurethanes, polystyrenes, polyvinyl alcohols, caprolactams, and copolymers of the foregoing.

Nonwoven webs that can be employed as the nonwoven top and bottom layers can be formed by a variety of known forming processes, including spunbonding, airlaying, meltblowing, or bonded carded web formation processes. For example, the top layer and bottom layer are both spunbond nonwoven webs, which have been found advantageous in forming barrier material.

Spunbond webs generally are stabilized or consolidated (pre-bonded) in some manner immediately as they are produced in order to give the web sufficient integrity and strength to withstand the rigors of further processing. This pre-bonding step may be accomplished through the use of an adhesive applied to the filaments as a liquid or powder which may be heat activated, or more commonly, by an air knife or compaction rolls. As used herein, the term "compaction rolls" means a set of rollers above and below the nonwoven web used to compact the web as a way of treating a just produced, meltspun filament, particularly spunbond, web, in order to give the web sufficient integrity for further processing, but not the relatively strong bonding of later applied, secondary bonding processes, such as through-air bonding, thermal bonding, ultrasonic bonding and the like. Compaction rolls slightly squeeze the web in order to increase its self-adherence and thereby its integrity. An air knife, directs heated air through a slot or row of openings onto the web to compact and provide initial bonding.

An exemplary secondary bonding process utilizes a patterned roller arrangement for thermally bonding the spunbond web. The roller arrangement typically includes a patterned bonding roll and a smooth anvil roll which together define a thermal patterning bonding nip. Alternatively, the anvil roll may also bear a bonding pattern on its outer surface. The pattern roll is heated to a suitable bonding temperature by conventional heating means and is rotated by conventional drive means, so that when the spunbond web passes through the nip, a series of thermal pattern bonds is formed. Nip pressure within the nip should be sufficient to achieve the desired degree of bonding of the web, given the line speed, bonding temperature and materials forming the web. Percent bond areas within the range of from about 10 percent to about 30 percent are typical for such spunbond webs.

The middle breathable film layer can be formed of any microporous film that can be suitably bonded or attached to top and bottom layers to yield a barrier material having the unique combination of performance characteristics and features described herein. A suitable class of film materials includes at least two basic components: a thermoplastic polyolefin polymer and a filler. These (and other) components can be mixed together, heated and then extruded into a mono-layer or multi-layer film using any one of a variety of film-producing processes known to those of ordinary skill in the film processing art. Such film-making processes include, for example, cast embossed, chill and flat cast, and blown film processes.

Generally, on a dry weight basis, based on the total weight of the film, the middle breathable film layer will include from about 30 to about 60 weight percent of the thermoplastic polyolefin polymer, or blend thereof, and from about 40 to about 70 percent filler. Other additives and ingredients may be added to the film layer provided they do not significantly interfere with the ability of the film layer to function in accordance with the teachings of the present invention. Such additives and ingredients can include, for example, antioxidants, stabilizers, and pigments.

In addition to the polyolefin polymer, the middle breathable film layer also includes a filler. As used herein, "filler" is meant to include particulates and other forms of materials which can be added to the film polymer extrusion blend and which will not chemically interfere with the extruded film but which are able to be uniformly dispersed throughout the film. Generally, the fillers will be in particulate form and may have a spherical or non-spherical shape with average particle sizes in the range of about 0.1 to about 7 microns. Both organic and inorganic fillers are contemplated to be within the scope of the present invention provided that they do not interfere with the film formation process, or the ability of the film layer to function in accordance with the teachings of the present invention. Examples of suitable fillers include calcium carbonate ($CaCO_3$), various kinds of clay, silica ($SiO_2$), alumina, barium carbonate, sodium carbonate, magnesium carbonate, talc, barium sulfate, magnesium sulfate, aluminum sulfate, titanium dioxide ($TiO_2$), zeolites, cellulose-type powders, kaolin, mica, carbon, calcium oxide, magnesium oxide, aluminum hydroxide, pulp powder, wood powder, cellulose derivatives, chitin and chitin derivatives. A suitable coating, such as, for example, stearic acid, may also be applied to the filler particles.

As mentioned herein, the breathable film layer may be formed using any one of the conventional processes known to those familiar with film formation. The polyolefin polymer and filler are mixed in appropriate proportions given the ranges outlined herein and then heated and extruded into a film. In order to provide uniform breathability as reflected by the water vapor transmission rate of the film, the filler should be uniformly dispersed through-out the polymer blend and, consequently, throughout the film layer itself so that upon stretching pores are created to provide breathability. For purposes of the present invention, a film is considered "breathable" if it has a water vapor transmission rate of at least 300 grams per square meter per 24 hours ($g/m^2/24$ hours). Generally, once the film is formed, it will have a weight per unit area of less than about 80 grams per square meter (gsm) and after stretching and thinning, its weight per unit area will be from about 10 gsm to about 25 gsm.

The breathable film layer used in the example of the present invention described below is a multi-layer film, however, other types, such as mono-layer films, are also considered to be within the scope of the present invention provided the forming technique is compatible with filled films. The film as initially formed generally is thicker and noisier than desired, as it tends to make a "rattling" sound when shaken. Moreover, the film does not have a sufficient degree of breathability as measured by its water vapor transmission rate. Consequently, the film is heated to a temperature equal to or less than about 5 degrees C. below the melting point of the polyolefin polymer and then stretched using an in-line machine direction orientation (MDO) unit to at least about two times (2x) its original length to thin the film and render it porous. Further stretching of the middle breathable film layer, to about three times (3x), four times (4x), or more, its original length is expressly contemplated in connection with forming the middle breathable film layer. After being stretch-thinned, the middle breathable film layer should have an "effective" film gauge or thickness of from about 0.2 mil to about 0.6 mil. The effective gauge is used to take into consideration the voids or air spaces in breathable film layers.

Cuffs are also desirably used in the present workwear or medical garments, and such cuffs are attached to the wrist end or sleeve edge of each sleeve. Cuffs may also be attached to the garment at the end of each pant leg, the neck of each garment, or as a waist band of shirt and/or pants, and so forth (not shown). Such cuffs are desirably made from elastic yarns formed from synthetic or natural materials. An example of a synthetic material for forming the elastic yarns is polyurethane. Spandex is an example of polyurethane-based elastomer. More particularly, spandex is a polyurethane in fiber form, containing a thermoplastic polyurethane elastomer with at least 85% polyurethane content. Commercial examples of spandex include LYCRA, VYRENE, DORLASTAN, SPANZELLE and GLOSPAN. An example of a natural material for forming elastic yarns is natural rubber. Polyester, nylon, and combinations of any of the foregoing synthetic and/or natural elastic yarns may also be used. The use of these and other materials to construct sleeves and/or cuffs is disclosed in U.S. Pat. No. 5,594,955, which is incorporated by reference in its entirety herein.

In one embodiment, cuffs are desirably sewn, thermally bonded, ultrasonically bonded, adhesively attached, and so forth to the lower end or sleeve edge of a garment sleeve. Desirably, the cuffs are sewn onto the sleeve using a thread or yarn treated to be substantially repellant to low surface tension liquids. Desirably, the cuffs are also treated to be substantially repellant to low surface tension liquids as well.

In an alternate embodiment, the cuff, neck opening, or waist opening of such a garment may be further treated to include hydrophobic or other repellant coatings. Such repellant coatings include fluorochemical coatings such as those described in U.S. Pat. Nos. 5,151,321, 5,116,682, and 5,145,727, all of which are incorporated in their entirety by reference herein. Such a fluorochemical treatment of a cuff could be, without being limited thereto, a flourochemical emulsion of 2% weight TG-KC01 available from Daikin America, of Decatur Ala. and 0.25% 1-Octanol available from Sigma-Aldrich, and approximately 97.75% deionized water.

Although various embodiments of garment configurations have been described above, it should be understood, that workwear of the present invention may generally have any configuration desired, and need not contain all of the components described above.

The present invention may be better understood with reference to the following examples, which are not meant to be limiting.

EXAMPLE

Material Example

In an example of the structure and method of making the structure, a line approximately one quarter inch across that tapered to one sixteenth of an inch across was produced on nonwoven medical gown material using a hot melt wax ink with a melting point of 125° C. and a Spectra Nova piezo-crystal printhead. (the GALAXY PH 256/80 HM) In particular, the material was cut from a roll of fabric (MicroCOOL, available from Kimberly-Clark Corporation, Roswell, Ga.) using a hydraulic press. The fabric described above in detail and in U.S. Pat. No. 6,037,281 was a three-layer laminate of spunbond material (SB), breathable film, and an SMS laminate. The body side or inside surface of the fabric was a 0.75 osy SMS and the exterior or outside surface was a 0.6 osy SB both made of polypropylene. The middle layer of the laminate was a cast film consisting of polypropylene skins and a linear low density polyethylene (LLDPE) core all filled with $CaCO_3$ and stretched to generate micropores for breathability. The ink containing the wax consisted of a commercially available ink from Markem Corporation (Hot Melt Ink, 5001 series, black). The add-on in this sample, that is the amount of wax actually applied to the nonwoven, was approximately 450 (between 450–500) grams per square meter (gsm) of treated fabric.

The width of the treatment zone, amount of wax add-on, and chemistry of the wax required to provide adequate anti-wicking properties will depend on the actual non-woven materials to be treated and the low surface tension liquid to be blocked. The treatment pattern can be any pattern, but is desirably continuous/solid lines such that it completely encircles/circumscribes the garment surrounding the covered limb. In the first example, a low surface tension liquid (32 dynes/cm) comprising 20% isopropyl alcohol colored with red food coloring (to allow for clear visualization), was placed in drop form immediately to one side of the printed line. At a line thickness of greater than about one eighth of an inch, wicking of liquid was prevented.

Figure 5:
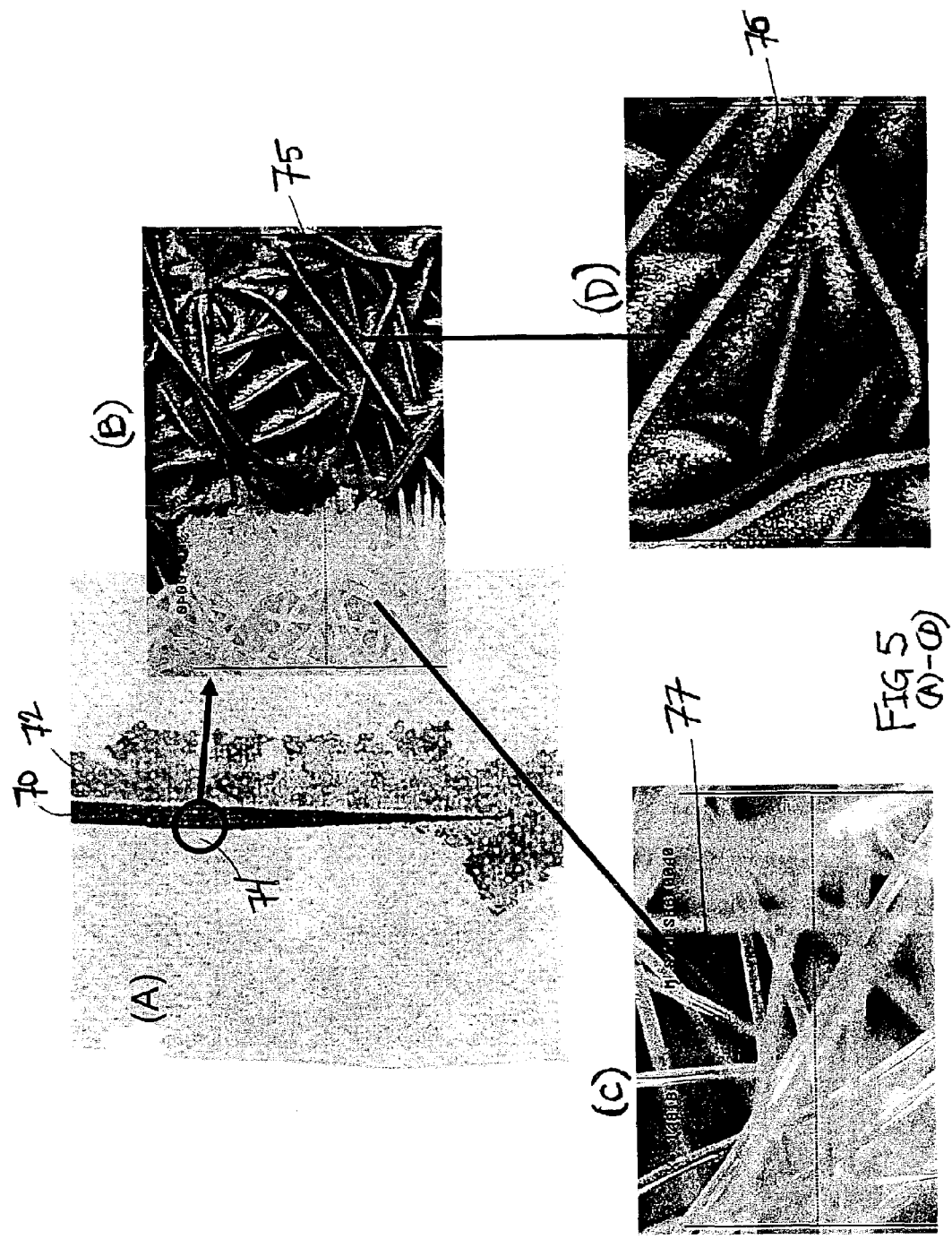
FIGS. 5A–5D illustrate photographic images of ink jet treated nonwoven fabric in accordance with the present invention.

As can be seen in FIGS. 5A through 5D, which present a photographic illustration of this example, a nonwoven material treated with a tapered line 70 of wax ink is shown. In FIG. 5A, it can be seen that the wax, when applied in a thick enough line, stops the wicking of such liquids 72 along the fibers of the nonwoven material. As can be seen in FIG. 5B, which is a close-up of area 74 of FIG. 5A, a colored wax film 75 covers those nonwoven fibers in the printed line region 70. As can be seen in FIGS. 5C and 5D, this colored wax film 75, extends between the fibers 76 in the treated region, but is clearly absent in the untreated region 77. The untreated nonwoven 77 has a surface morphology that is open, porous, and more conducive to wicking of liquids. In FIG. 5D, this pore structure has been collapsed and clogged in the wax treated region, providing a barrier to wicking of liquids.

Three additional samples at three sets of conditions (for a total of nine samples) were produced under the following conditions to measure the effects of ink add-on in the treated region:

Pattern: 40 MID. Jet (40 jets firing)
Throw Distance: 3 mm
Printhead Angle Relative to Substrate: approximately 74°
Printed Line Thickness: approximately $\frac{1}{8}^{th}$ of an inch
Line Speed: 6 feet per minute on rotary drum.
Ink: Markem 5001 series, black.
Fire Frequencies: 4, 6, 8 kHz (3 samples at each)

Approximate Ink Add-on Levels: 150 gsm, 225 gsm, 300 gsm (3 samples at each)

In the three samples printed with a $\frac{1}{8}^{th}$ inch line at 150 gsm add-on, only one prevented the low surface tension fluid described above from wicking across the printed region. In all the samples printed with a $\frac{1}{8}^{th}$ inch line at 225 gsm and 300 gsm add-on levels, the low surface tension fluid was blocked from wicking across the pattern. These tests were then repeated while placing the samples on a 45 degree slant to investigate if gravity may help drive the fluid through the treated regions. The results obtained, however, were identical to those obtained on a horizontal surface. Namely, the 225 gsm and 300 gsm ink patterns prevented fluid from wicking downhill across the treated regions.

While the present invention has been described in connection with certain desired embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. Protective outerwear for covering a body portion, said protective outerwear having one or more layers and having an inside surface and an outside surface, said outside surface including thereupon a printed blocking material in a continuous unbroken band, region, or combination of such through the thickness of one or more of the layers, for blocking the wicking of low surface tension liquid at least on said outside surface of said outerwear, wherein said protective outerwear is a medical garment selected from the group consisting of hospital gowns, surgical gowns, and medical scrubs, and further wherein said hospital gowns, surgical gowns, and medical scrubs have sleeve portions, and neck portions.

2. The protective outerwear of claim 1 wherein said low surface tension liquid blocking material is present on said outside surface in multiple bands.

3. The protective outerwear of claim 1 wherein said low surface tension liquid blocking material is present on said outside surface in a region.

4. The protective outerwear of claim 1 wherein said low surface tension liquid blocking material is present on said outside surface in at least a band and a region.

5. The protective outerwear of claim 1 wherein said low surface tension liquid blocking material is present in a band having a width between about $\frac{1}{8}$ to 1 inch.

6. The protective outerwear of claim 1 wherein said low surface tension liquid blocking material is present in a band having a width between about $\frac{1}{8}$ to $\frac{1}{2}$ inch.

7. The protective outerwear of claim 1, wherein said outerwear is comprised of a nonwoven material and further, wherein said outerwear also includes bonded bands, formed from said nonwoven material, for blocking low surface tension liquids from wicking on the outside surface of said outerwear, by sealing or closing pores in said nonwoven material.

8. The protective outerwear of claim 1, wherein said low surface tension blocking material is printed on said medical garment in the sleeve or neck portion.

9. A protective outerwear garment having an inside surface and an outside surface comprising:
a body portion;
a neck portion;
two sleeves attached to the body, each sleeve having one or more layers and having an inside surface and an outside surface, each sleeve comprising a lower edge for encircling a use's wrist and hand, an elbow region for containing a user's elbow, and an upper edge attached to said body portion,
wherein said sleeves include at least along their outside surfaces a printed blocking material in a continuous unbroken band, region, or combination of such through the thickness of one or more of the layers, for blocking the wicking of low surface tension liquid on at least said outside surface of said outerwear.

10. The protective outerwear garment of claim 9 wherein said low surface tension liquid blocking material is located on said sleeves between the sleeve lower edge and the elbow region.

11. The protective outerwear garment of claim 9 wherein said low surface tension liquid blocking material is located adjacent the neck portion along the garment outside surface.

12. The protective outerwear of claim 9 wherein said low surface tension liquid blocking material is present on said outside surface of said sleeves in multiple bands.

13. The protective outerwear of claim 9 wherein said low surface tension liquid blocking material is present on said outside surface of said sleeves in a region.

14. The protective outerwear of claim 9 wherein said low surface tension liquid blocking material is present on said outside surface of said sleeves in at least a band and a region.

15. The protective outerwear of claim 9, wherein said protective outerwear is a medical garment.

16. The protective outerwear of claim 15, wherein said medical garment is selected from the group consisting of hospital gowns, surgical gowns, and medical scrubs.

17. The protective outerwear of claim 9, wherein said protective outerwear is comprised of a nonwoven material and is provided with a bonded region for blocking low surface tension liquid, said bonded region formed from said nonwoven material.

18. The protective outerwear of claim 17 wherein said bonded region is created by either thermal bonding or ultrasonic bonding.

19. The protective outerwear of claim 9, wherein said protective outerwear is comprised of a nonwoven material and wherein a portion of said nonwoven material is overlapped on another portion and said portions are bonded together to provide a bonded region for blocking the wicking of low surface tension liquid.

20. The protective outerwear of claim 19, wherein said overlapped portions provide a packet.

21. The protective outerwear of claim 9 further including cuffs attached at least at the lower edge of each sleeve, the cuffs treated to block wicking of fluids.

22. Protective outerwear for covering a body portion, said protective outerwear having one or more layers and having an inside surface and an outside surface, said outside surface including thereupon a printed blocking material in a continuous unbroken band, region, or combination of such through the thickness of one or more of the layers, for blocking the wicking of low surface tension liquid at least on said outside surface of said outerwear, wherein said low surface tension liquid blocking material is present on said outside surface in multiple bands.

23. Protective outerwear for covering a body portion, said protective outerwear having one or more layers and having an inside surface and an outside surface, said outside surface including thereupon a printed blocking material in a continuous unbroken band, region, or combination of such through the thickness of one or more of the layers, for blocking the wicking of low surface tension liquid at least on said outside surface of said outerwear, wherein said low surface tension liquid blocking material is present on said outside surface in at least a band and a region.

24. Protective outerwear for covering a body portion, said protective outerwear having one or more layers and having an inside surface and an outside surface, said outside surface including thereupon a printed blocking material in a continuous unbroken band, region, or combination of such through the thickness of one or more of the layers, for blocking the wicking of low surface tension liquid at least on said outside surface of said outerwear, wherein said low surface tension liquid blocking material is present in a band having a width between about 1/8 to 1 inch.

25. Protective outerwear for covering a body portion, said protective outerwear having one or more layers and having an inside surface and an outside surface, said outside surface including thereupon a printed blocking material in a continuous unbroken band, region, or combination of such through the thickness of one or more of the layers, for blocking the wicking of low surface tension liquid at least on said outside surface of said outerwear, wherein said outerwear is comprised of a nonwoven material and further, wherein said outerwear also includes bonded bands, formed from said nonwoven material, for blocking low surface tension liquids from wicking on the outside surface of said outerwear, by sealing or closing pores in said nonwoven material.

* * * * *